(12) United States Patent
Choe et al.

(10) Patent No.: US 7,033,583 B2
(45) Date of Patent: Apr. 25, 2006

(54) POLYMERIC THIOL-LINKED PRODRUGS

(75) Inventors: Yun H. Choe, Green Brook, NJ (US); Richard B. Greenwald, Somerset, NJ (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 51 days.

(21) Appl. No.: 10/290,695

(22) Filed: Nov. 8, 2002

(65) Prior Publication Data

US 2003/0147844 A1     Aug. 7, 2003

Related U.S. Application Data

(60) Provisional application No. 60/367,320, filed on Mar. 25, 2002, provisional application No. 60/344,914, filed on Nov. 9, 2001.

(51) Int. Cl.
*A61K 31/74* (2006.01)
*A61K 31/75* (2006.01)

(52) U.S. Cl. ..................................... 424/78.1
(58) Field of Classification Search ................ 514/279, 514/283; 549/510, 511; 528/421; 546/48, 546/51
See application file for complete search history.

(56) References Cited

U.S. PATENT DOCUMENTS 3,901,930 A * 8/1975 Wirth et al. .................. 556/86
5,112,739 A    5/1992 Meneghini et al.
5,840,900 A * 11/1998 Greenwald et al. ............ 546/48

FOREIGN PATENT DOCUMENTS

WO    WO/00/67801       11/2000
WO    WO 200067801 A2 * 11/2000

OTHER PUBLICATIONS

R Roy, et al. Synthesis of hyper-branched dendritic lactosides. (1995) Tetrahedron Letters, 36, 4377-4380.*
Woghiren, Clement, et al. Protected Thiol-Polyethylene Glycol: A New Activated Polymer for Reversible Protein Modification, Bioconjugate Chem. 1993, 4, 314-318.
Modica, Emilia et al., Alkylation of Amino Acids and Glutathione in Water by o-Quinone Methide. Reactivity and Selectivity, J. Org. Chem. 2001, 66, 41-52.
Bogardus, Joseph B., et al., Kinetics and Mechanism of Hydrolysis of Labile Quaternary Ammonium Derivatives of Tertiary Amines, Journal of Pharmaceutical Sciences, Jul. 1982, vol. 71 no. 7.
Harada, Naoyuki et al., Water-Soluble Antitumor Agents. I. Synthesis and Biological Activity of 6-S-Aminoacyloxymethyl Mercaptopurine Derivatives, Chem. Pharm. Bull. 43(10) 1793-1796 (1995).
Kashida, Tatsuo, Augmentation of Sinecomitant Immunity in Mice by y-(9H-Purine-6-yl) thiomethyl L-Glutamate (6-MPG), a Water-Soluble Derivative of 6-Mercaptopurine, Biol. Pharm. Bull. 21(1) 16-21 (1998).
Taylor, Lloyd D., Use of o-and p-Hydroxybenzyl Functions as Blocking Groups Which Are Removable with Base, J. Org. Chem., vol. 43, No. 6, 1978.
Wakselman, Michel, 1,4-And 1,6-Eliminations From Hydroxy- And Amino-Substituted Benzyl Systems: Chemical and Biochemical Applications, Nouveau Journal De Chime, vol. 7 7-1983 p. 439-447.

* cited by examiner

*Primary Examiner*—Bruce R. Campell
*Assistant Examiner*—Andrew D. Kosar
(74) *Attorney, Agent, or Firm*—Lucas & Mercanti, LLP

(57) ABSTRACT

Thiol-linked polymeric prodrugs and methods of making and using the same are disclosed. The use of a sulfhydryl bond as the basic link for linking the polymer to the drug allows a prodrug to be formed which takes advantage of plasma enzymes in vivo. A preferred conjugate is

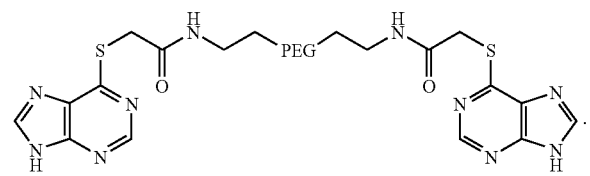

Methods of preparing and treatment are also disclosed.

19 Claims, 11 Drawing Sheets

A.

POLYMERIC THIOL-LINKED PRODRUGS

CROSS-REFERENCE TO RELATED APPLICATIONS

This application claims the benefit of priority from U.S. Provisional Patent applications 60/344,914, filed Nov. 9, 2001 and U.S. Provisional Patent applications 60/367,320, filed Mar. 25, 2002. The contents of each provisional application are incorporated herein by reference.

TECHNICAL FIELD

The present invention relates to new types of long-acting, thiol-linked polymer conjugates of biologically-effective materials. In particular, the invention relates to polymer-based prodrug conjugates having enhanced water solubility, controlled pharmacokinetics and improved bioavailability, relative to the unmodified bioactive materials.

BACKGROUND OF THE INVENTION

Over the years, several methods of administering biologically-effective materials to animals have been proposed. Many biologically-effective materials are available as water-soluble salts and can be readily included as medicinal agents in pharmaceutical formulations. Problems arise when the desired biologically-effective material is either poorly soluble in aqueous fluids or is rapidly degraded in vivo. Simply by way of example, many of these biologically-effective materials have mercapto-functional groups. These include e.g., antiproliferative and/or immunosuppressive agents such as the mercaptopurines, as well as peptides and proteins with demonstrated or potential utility as medicinal agents. These types of materials often present complex problems of pharmacokinetics and bioavailability based on their poor solubility in blood or tissue fluids, tissue distribution, clearance rate and antigenicity, after administration to an animal in need of such treatment.

For instance, the class of compounds known as nucleoside and nucleotide analogs are potentially useful therapeutically in the treatment of cancers and in immuno-supression, because they interfere with DNA synthesis. This property is useful in treating a broad class of diseases or disorders characterized by excessive or inappropriate cell division. However, the artisan will appreciate that these compounds have a very narrow therapeutic index, requiring careful control of dose, kinetics and tissue concentrations. Thus, there is a need to provide improved nucleoside and nucleotide analogs where more targeted delivery to selected tissues, and/or improved release kinetics is desirable.

For example, 6-mercaptopurine or 6-MP, while otherwise a promising anticancer agent and immunosuppressive, has substantial drawbacks. Absorption of 6-MP is incomplete after oral ingestion and bioavailability is reduced by first-pass metabolism through the liver. It is reported that oral bioavailability of 6-MP is only 5% to 37%, with great variability between patients.

One way to solubilize biologically-effective materials and improve solubility, bioavailability, etc., is to include them as part of a soluble prodrug. Prodrugs include chemical derivatives of a medicinal agent, e.g., a biologically-effective parent compound which, upon administration, eventually liberates the parent compound in vivo. Prodrugs allow the artisan to modify the onset and/or duration of action of an agent, in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols.

Prodrugs are often biologically inert or substantially inactive forms of the parent or active compound. The rate of release of the active drug, typically by hydrolysis, is influenced by several factors, but especially by the type of bond joining the parent drug to the modifier. Care must be taken to avoid preparing prodrugs which are eliminated through the kidney or reticular endothelial system, etc., before a sufficient amount of hydrolysis of the parent compound occurs.

Previous efforts to improve the utility of certain therapeutically useful mercaptan compounds have been reported. For example, azathioprine (IMURAN) is a prodrug of 6-mercaptopurine containing an imidazole group attached to the sulfur at the 6-position of the purine ring. This substitution serves to decrease the rate of inactivation by enzymatic S-methylation, nonenzymatic oxidation, and/or conversion to thiourate by xanthine oxidase. Azathioprine reacts with sulfhydryl compounds such as glutathione (reported to be by nonenzymatic pathways) which produces a more controlled liberation of mercaptopurine in tissues. Azathioprine is also reported to provide enhanced immunosuppressive activity relative to unmodified 6-MP. In spite of this advance, further improvements have been sought in order to deliver various mercaptan-based therapeutic agents in ways which would be therapeutically superior to that which is currently available. For example, it would be desirable to reduce the number of dosages a patient would require and/or more predictable control of the rate of release of the drug from a carrier.

Incorporating a polymer as part of a prodrug system has been suggested to increase the circulating life of some drugs having an available hydroxyl or amine group. See, for example U.S. Pat. No. 6,180,095, the contents of which are incorporated herein by reference. The '095 patent discloses polymer-based double prodrug systems using a benzyl elimination (BE) system for controllably delivering biologically active materials in vivo.

While a number of polymeric prodrug systems are known to the art, including those prepared by linking a polyethylene glycol (PEG) to a drug or other agent of interest, conjugates that directly exploit the thiol function groups of many potentially useful biologically effective substances are not believed to be mentioned. Protected sulfur-linked polyethylene glycols are also known, although these ultimately form polymer-drug conjugates via covalent disulfide bonds (—S—S— bonds) not via covalent thiol bonds (—SH— bonds). See Woghiren et al., 1993, *Bioconjugate Chem.* 4: 314–318, who linked a 5 kDa PEG to papain enzyme by disulfide linkers.

Thus, there remains a need for improved polymeric prodrug systems for thiol- or mercaptan containing compounds. The present invention addresses this need.

SUMMARY OF THE INVENTION

In one aspect of the invention, compounds of Formula (I) are provided:

$$R_1\text{-}E \qquad (I)$$

wherein:

$R_1$ is a straight or branched residue of a water soluble polymer;

E is

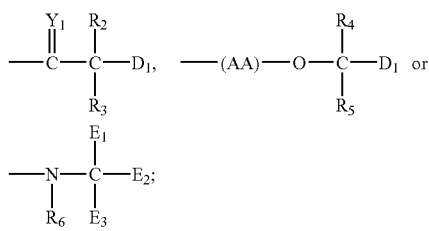

wherein:
D₁ is residue of a —SH containing moiety;
(AA) is an amino acid residue;

$E_1$ is

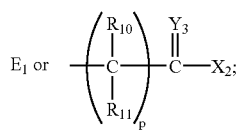

$E_2$ and $E_3$ are independently H, $E_1$ or $-\left(\begin{array}{c} R_{10} \\ | \\ C \\ | \\ R_{11} \end{array}\right)_p - \overset{Y_3}{\underset{\|}{C}} - X_2;$ $Y_1$, $Y_2$ and $Y_3$ are independently O, S or $NR_7$;
$X_1$ and $X_2$ are independently OH or E;
$R_2$, $R_3$, $R_4$, $R_5$, $R_6$, $R_7$, $R_8$, $R_9$, $R_{10}$ and $R_{11}$ are independently selected from the group consisting of H, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
n is zero or a positive integer; and
p is zero or a positive integer.

In alternative aspects of the invention there are provided methods of preparing the prodrug conjugates as well as methods of treatment using the same.

One advantage associated with the prodrugs of the present invention is the fact that the artisan is now capable of delivering mercaptan-based therapeutic compounds as of polymeric transport systems. By utilizing the sulfhydryl bond as the basis for linkage, the artisan can take advantage of the reactivity of such linkages to plasma enzymes in vivo.

Another advantage is that because the sulfhydral moiety is sometimes associated with the active site of a biologically active moiety, such as a cysteine residue of a polypeptide, the process of the present invention allows the activity to be selectively blocked for a predefined when such property is desirable.

DETAILED DESCRIPTION OF THE INVENTION

Figure 1:
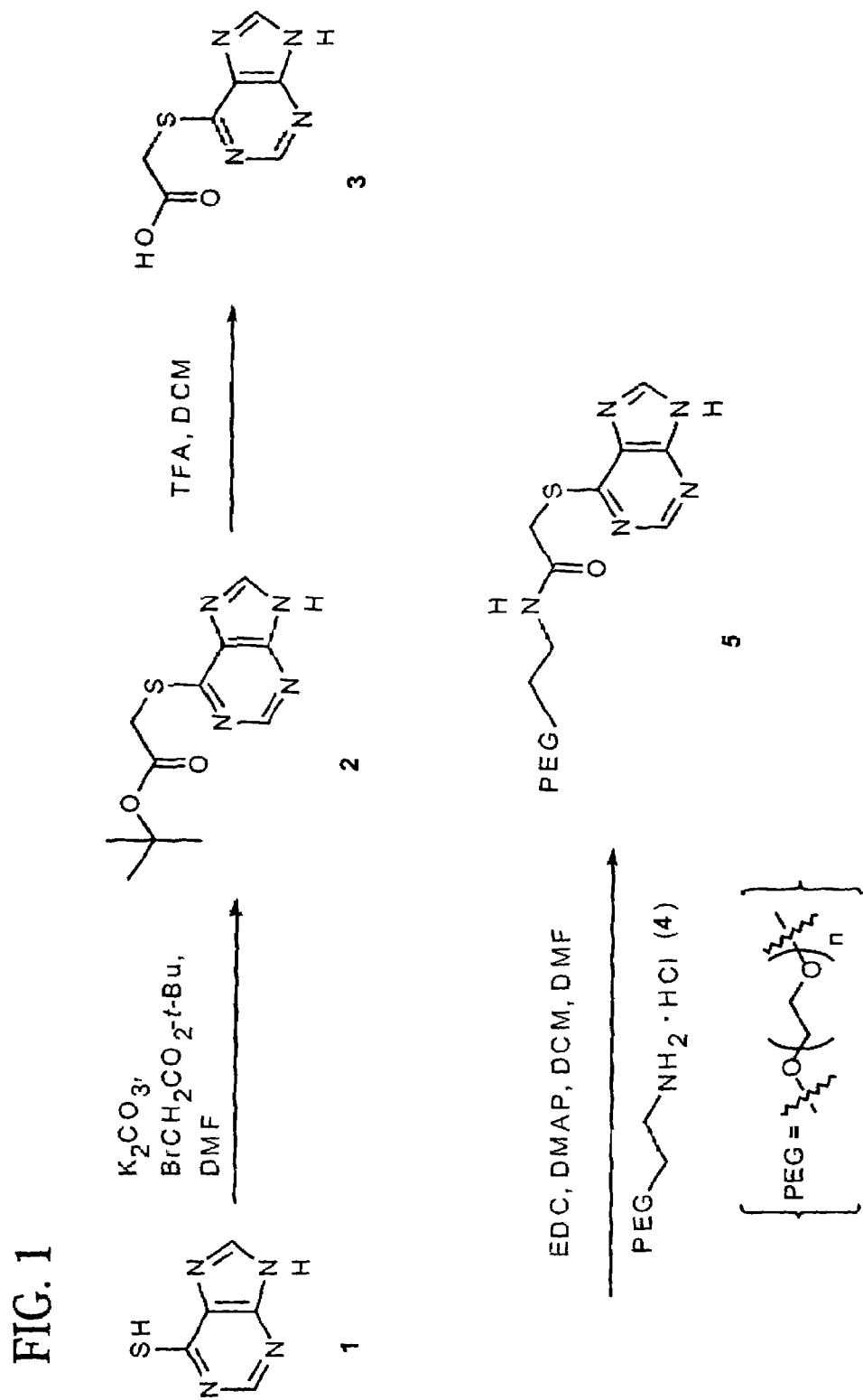
FIG. 1 illustrates the synthetic reactions described in Examples 1–3.
Figure 2:
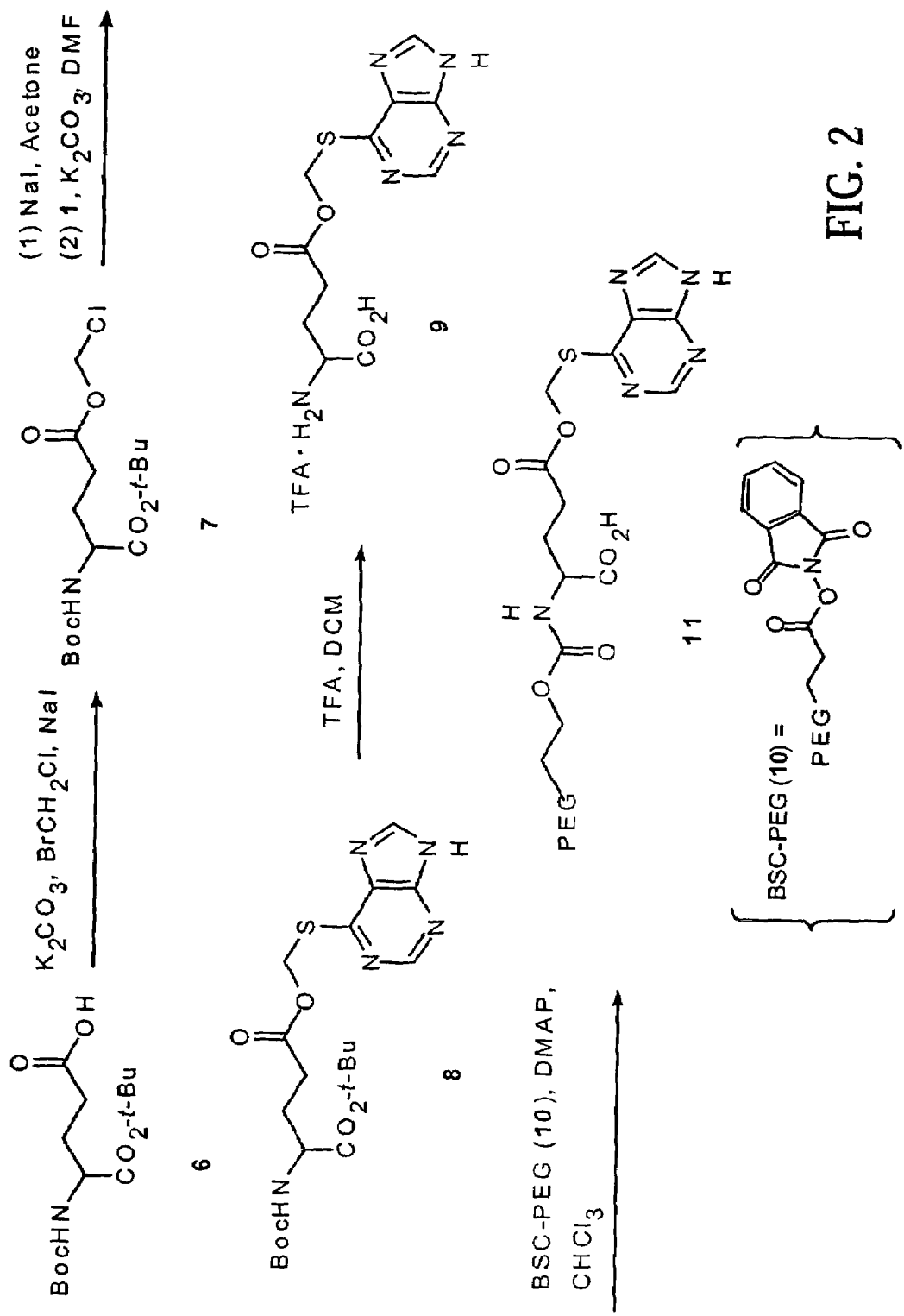
FIG. 2 illustrates the synthetic reactions described in Examples 4–7.
Figure 3A:
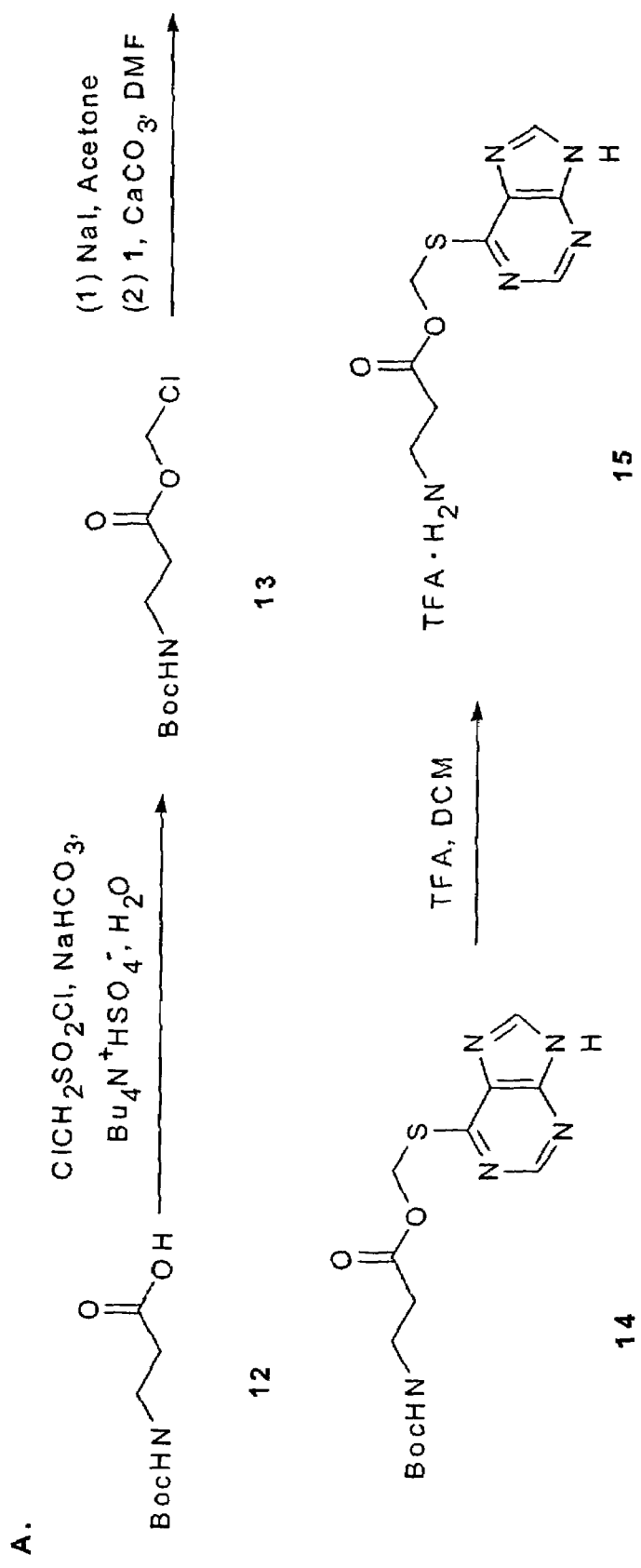
FIG. 3A illustrates the synthetic reactions described in Examples 8–10.
Figure 3B:
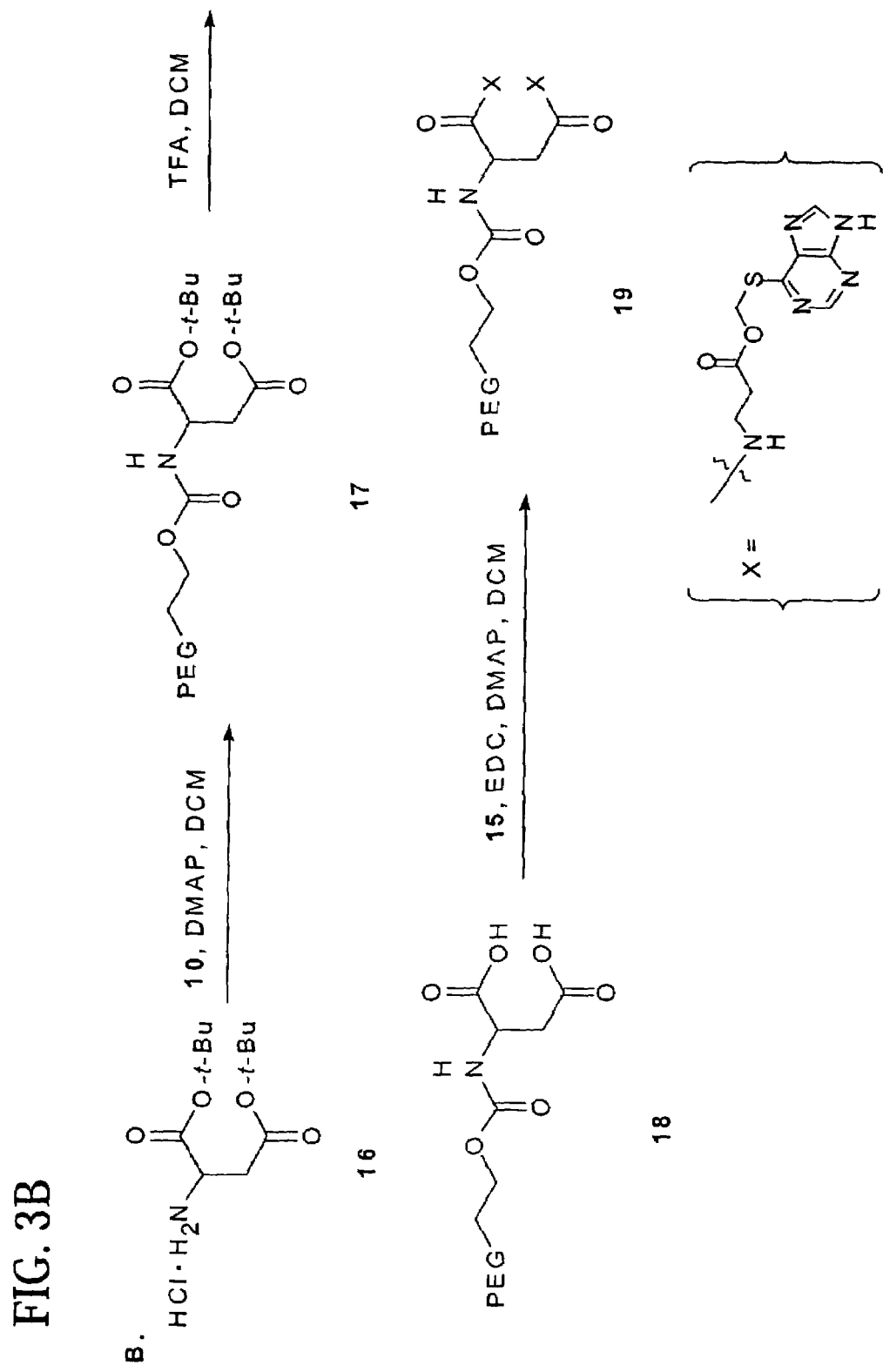
FIG. 3B illustrates the synthetic reactions described in Examples 11–13.
Figure 4:
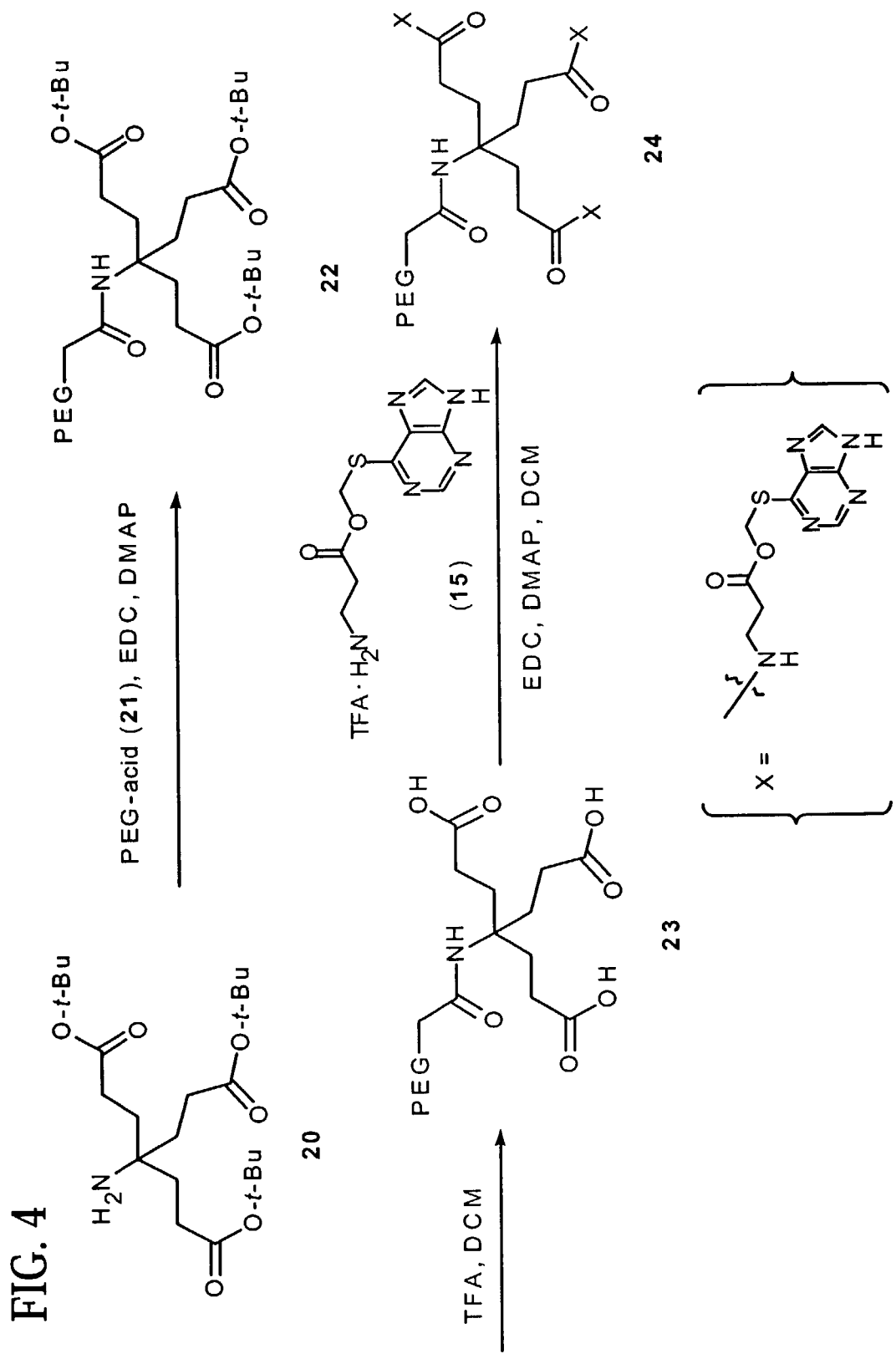
FIG. 4 illustrates the synthetic reactions described in Examples 14–16.
Figure 5A:
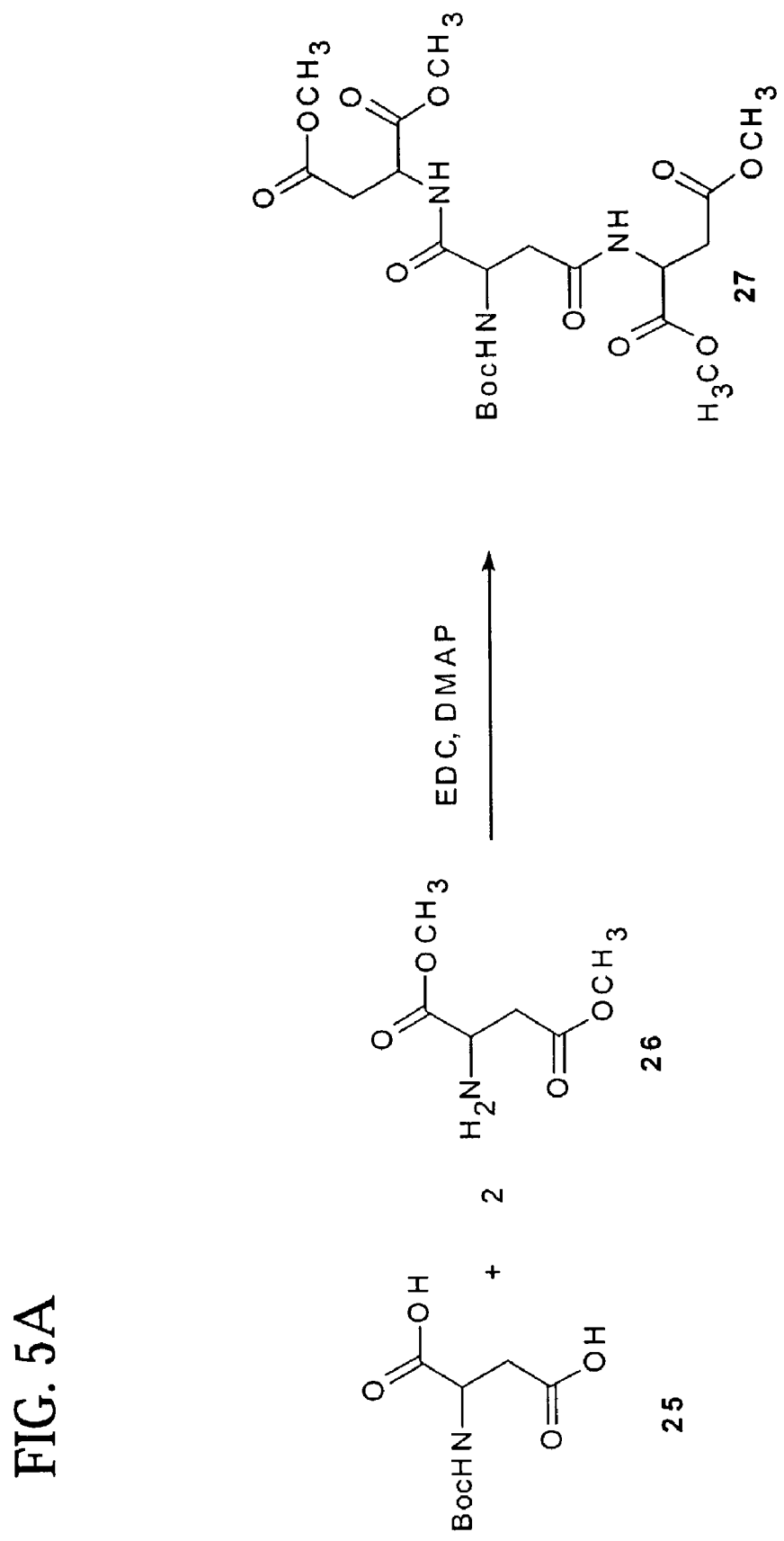
FIG. 5A illustrates the synthetic reaction described in Example 17.
Figure 5B:
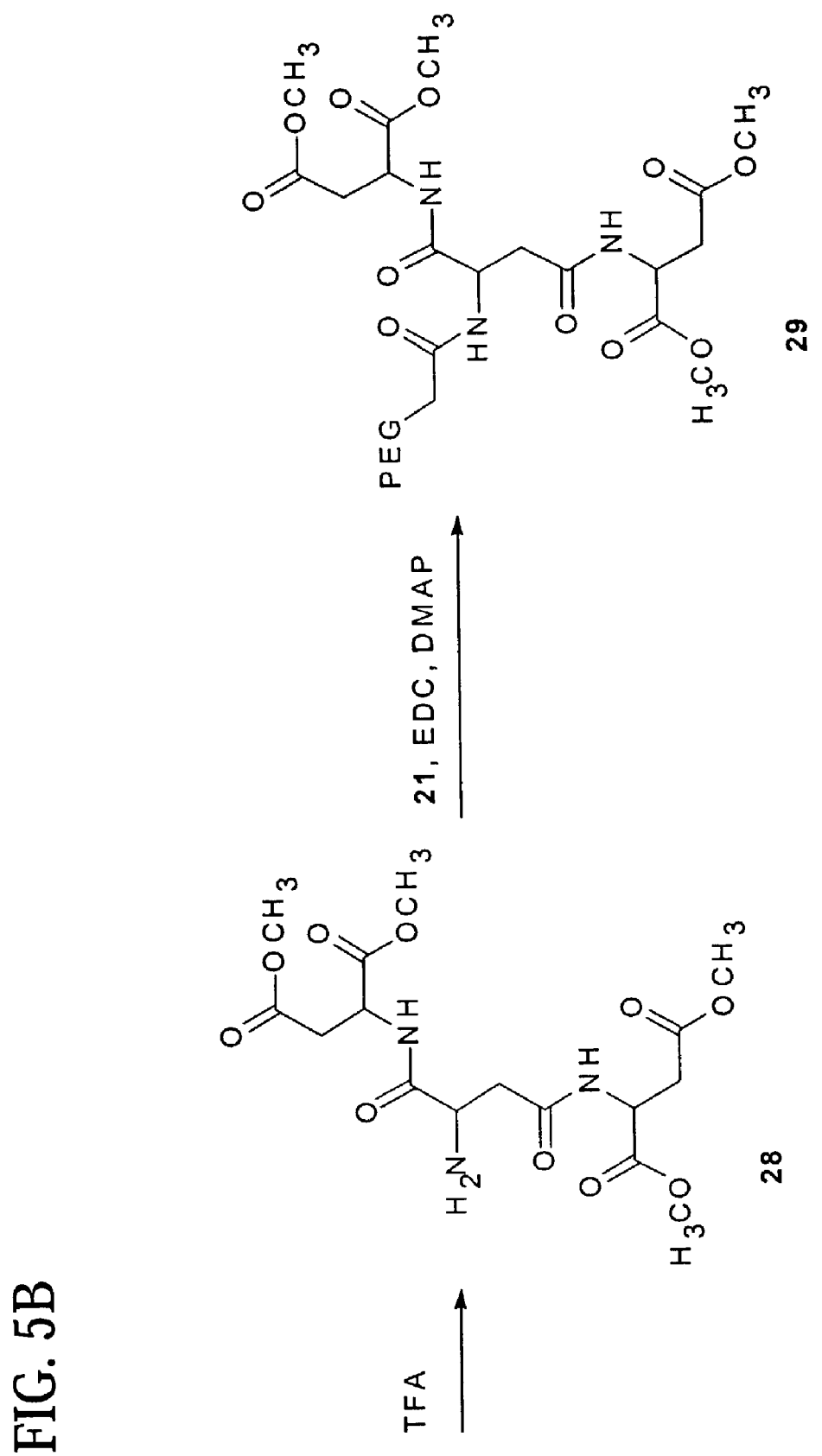
FIG. 5B illustrates the synthetic reactions described in Examples 18–19.
Figure 5C:
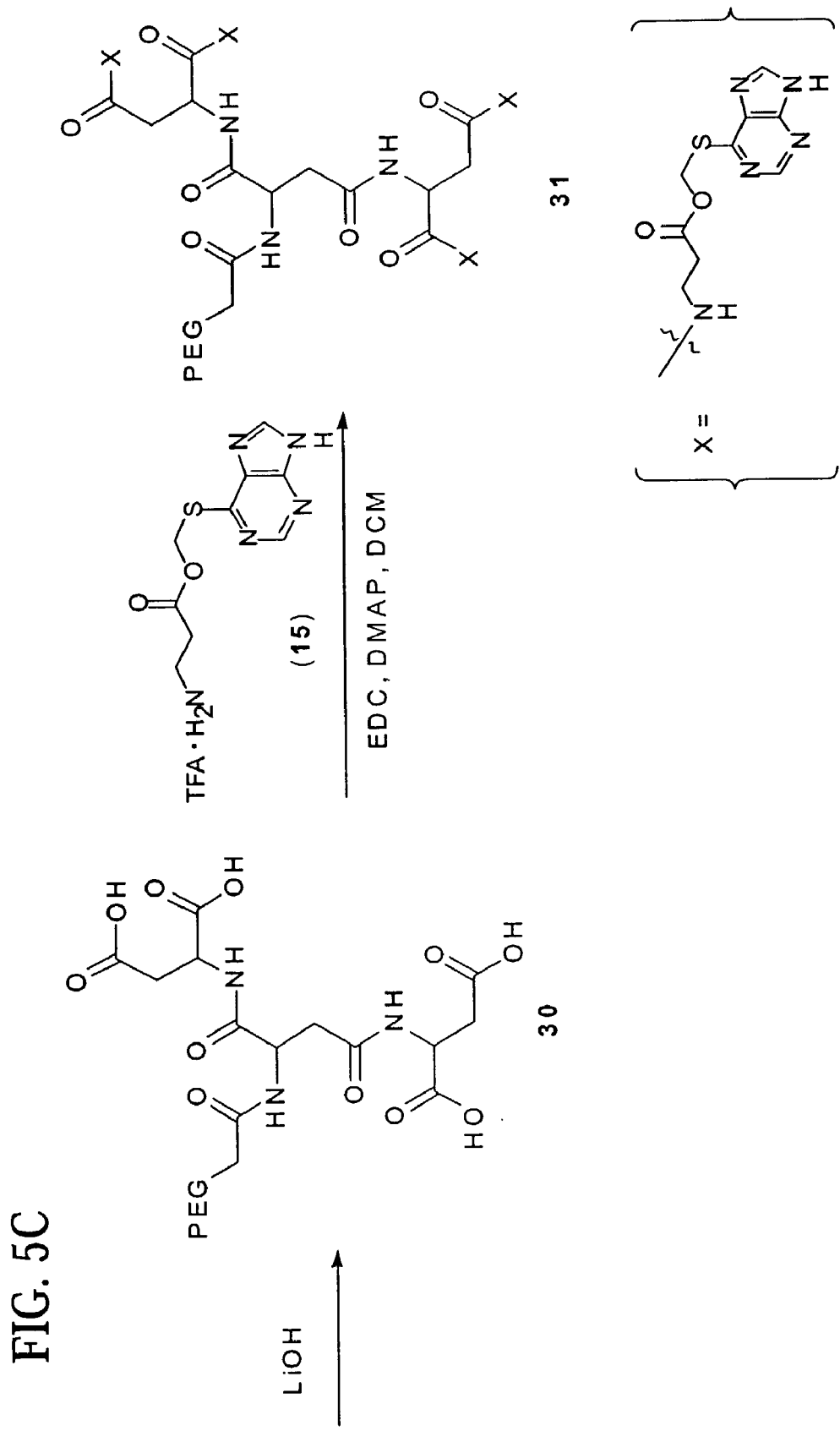
FIG. 5C illustrates the synthetic reactions described in Examples 20–21.
Figure 6A:
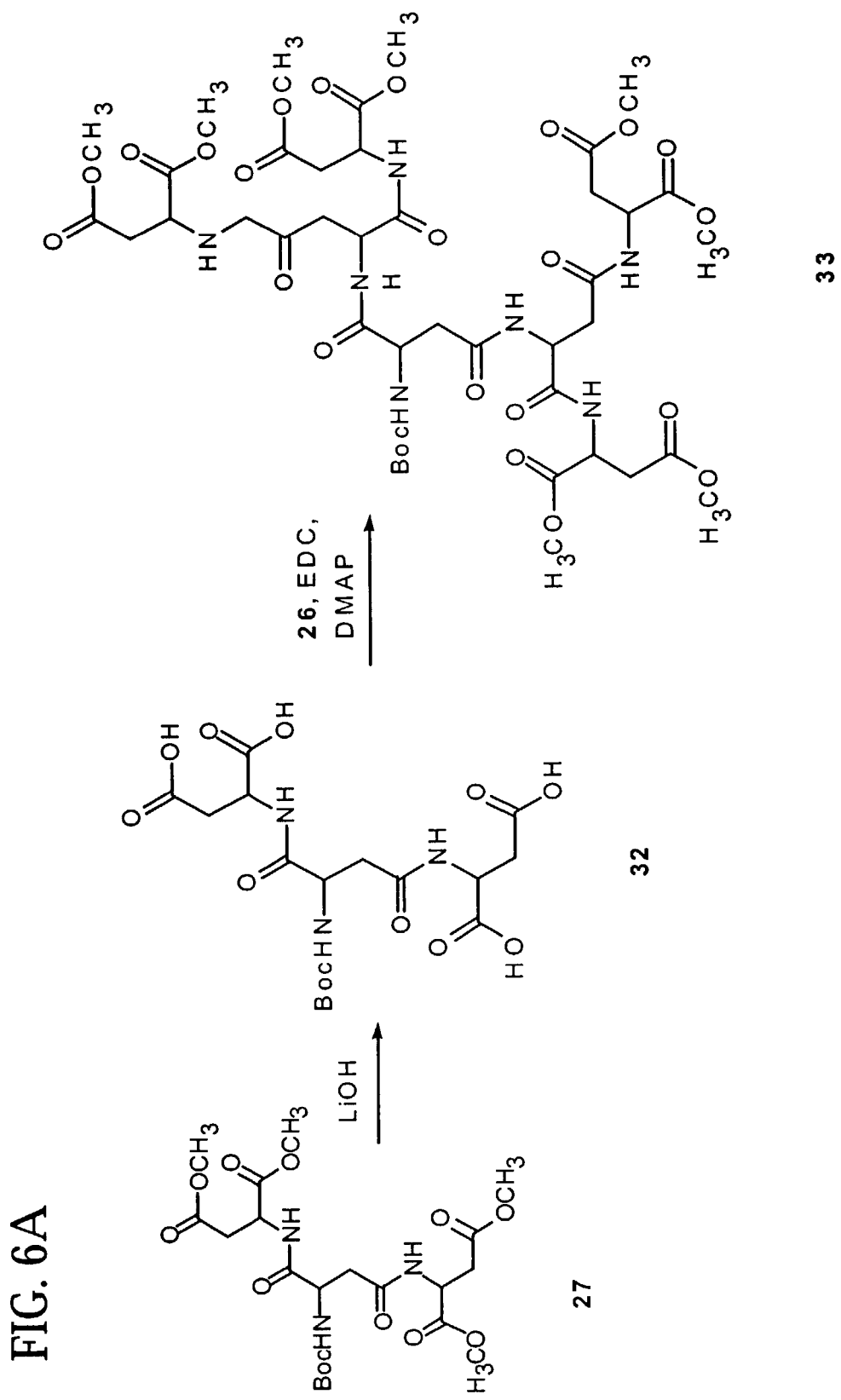
FIGS. 6A–6C illustrate synthetic reactions described in Examples 22–23.
Figure 6B:
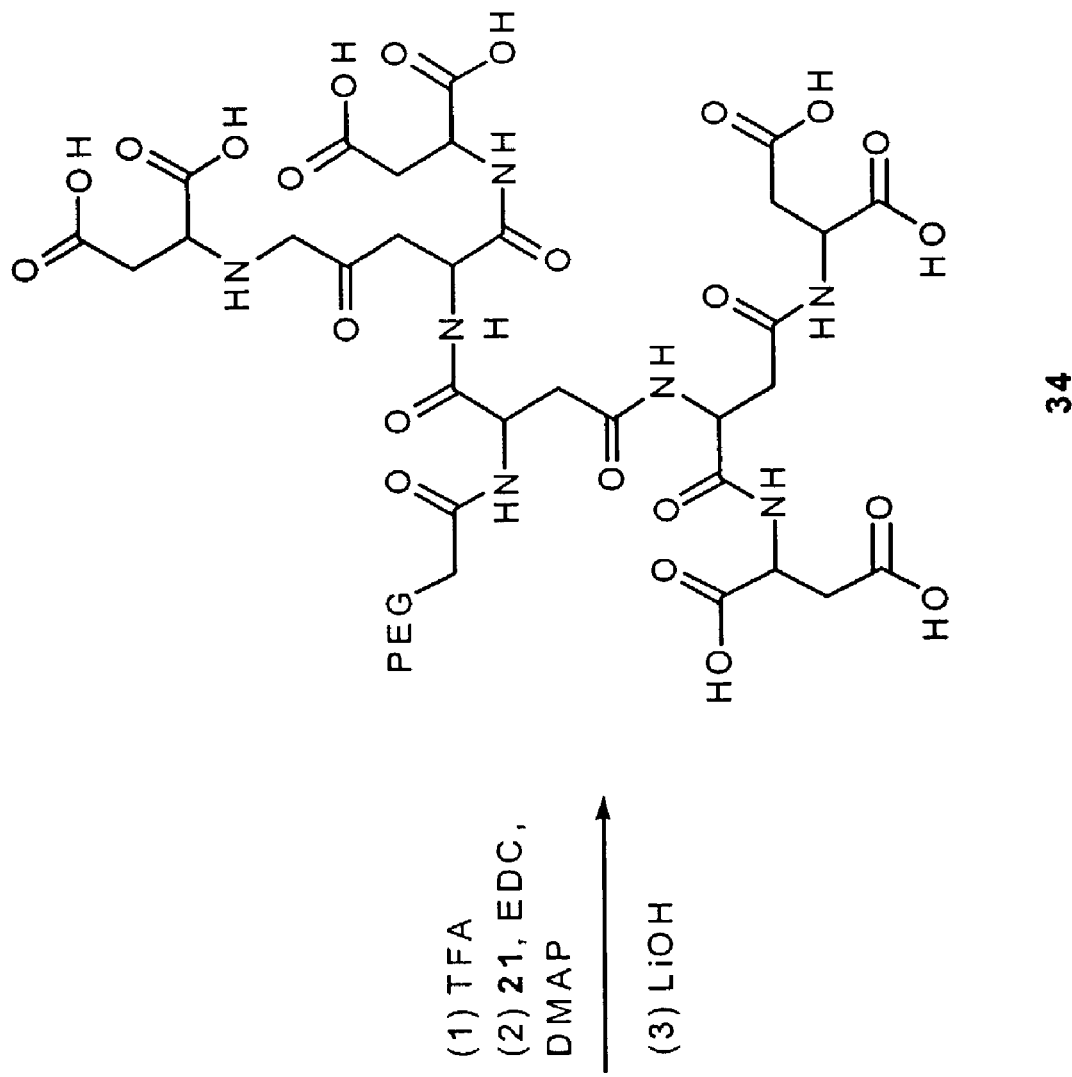
Figure 6C:
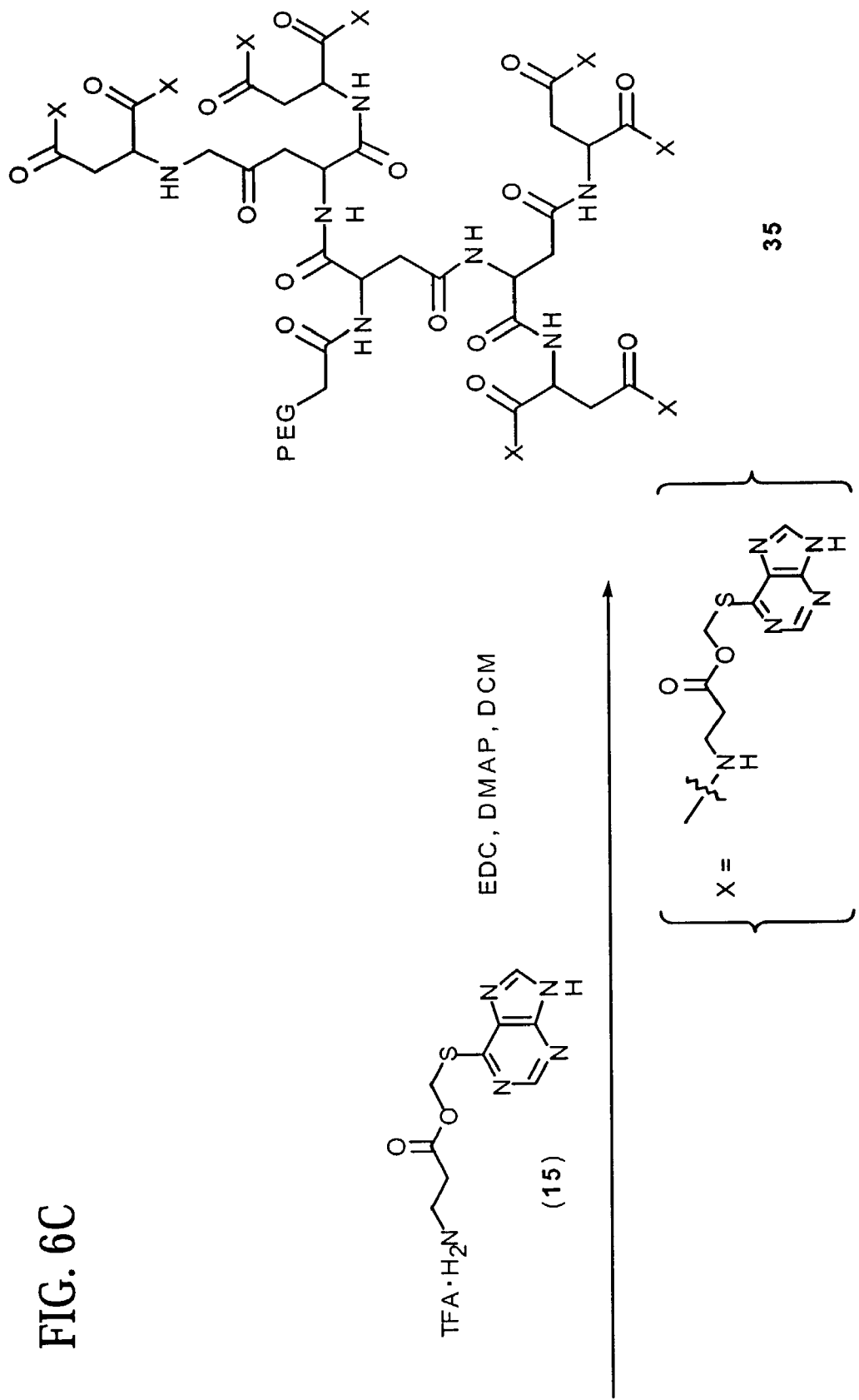

Accordingly, the invention provides for polymer conjugates, which are prodrugs formed by linking suitable water-soluble, substantially non-antigenic polymers to biologically effective compounds of interest, e.g., drugs and the like having an available mercapto-group which is capable of undergoing a reaction with an activated polymer. This is accomplished by forming covalent linkages to one or more suitable HS-functional groups present in such compounds.

In order that the reader better appreciate the description of the invention, the following definitions are provided.

For purposes of the present invention, the terms, "biologically effective material," "biologically active material," and "biologically active compound," and/or "biologically active agent," etc., are used interchangeably unless otherwise stated. These terms refer, for example, to a drug or pharmaceutical, and/or a diagnostic agent or reagent, such as a detectable label or marker, and are also used interchangeably with the terms, "agent," "medicinal agent," and "active agent," that may be employed herein. These terms all refer to compound(s) with a useful property or activity, particularly when administered to an animal, in vivo, and/or to precursors of the same, unless otherwise stated.

For purposes of the present invention, the use of the singular or plural is not meant to be limiting of the numerical number of the referenced item or object. Thus, the use of the singular to refer to a cell, polymer or drug does not imply that only one cell is treated, only one molecule is prepared or employed, and/or only one drug is employed, and the use of the plural does not exclude application to a single referenced item, unless expressly stated. Further to this point, for purposes of the present invention, the terms, "cell," "cell type," "target cell," and etc., are used interchangeably unless otherwise specified and refer to both singular and plural cells, however organized into a tissue, tissues or other system or component, normal or pathological, of an animal or patient to be treated.

For purposes of the present invention, the term "residue" shall be understood to mean that portion of a biologically effective compound or drug which remains after the compound has undergone a substitution reaction in which the prodrug carrier portion has been attached, preferably via a SH linkage. Analogously, a polymer residue is the portion of a polymer that remains after the linkage to a biologically effective compound of interest.

For purposes of the present invention, the term "alkyl" shall be understood to include, e.g., lower alkyl, straight, branched, substituted alkyl, e.g. halo-, alkoxy-, and nitro- $C_{1-12}$ alkyls, $C_{3-8}$ cycloalkyls or substituted cycloalkyls, etc. Lower alkyl shall be understood to be $C_{1-12}$, unless otherwise indicated.

For purposes of the present invention, the term "substituted" shall be understood to include adding or replacing one or more moieties contained within a functional group or compound with one or more different moieties. Optionally, an entire functional group is substituted.

For purposes of the present invention, substituted alkyls include carboxyalkyls, aminoalkyls, dialkylamino alkyls, hydroxyalkyls and mercaptoalkyls; substituted cycloalkyls include substituted haloalkyls, e.g., 4-chlorocyclohexyl; aryls include moieties such as naphthyl; substituted aryls include moieties such as 3-bromophenyl; aralkyls include, e.g. moieties such as toluenes; heteroalkyls include, e.g., moieties such as ethylthiophene; substituted heteroalkyls include, e.g., moieties such as 3-methoxy-thiophene; alkoxy includes, e.g., moieties such as methoxy; and phenoxy includes, e.g., moieties such as 3-nitrophenoxy. Halo- shall be understood to include fluoro, chloro, iodo and bromo.

The term "sufficient amounts" for purposes of the present invention shall mean an amount which achieves a desired effect, e.g., in a method of treatment this is a therapeutic effect, as such effect is understood by those of ordinary skill in the art.

A. Formula I

As pointed out in the Summary, in one embodiment of the invention, compounds corresponding to Formula I are preferred. In more preferred embodiments, $R_1$ is a bifunctionalized substantially non-antigenic polymeric residue containing a capping group designated herein as Z, which can be one of hydrogen, $NH_2$, OH, $CO_2H$, $C_{1-6}$ moieties and $$E'\text{-} \qquad (I')$$

wherein:

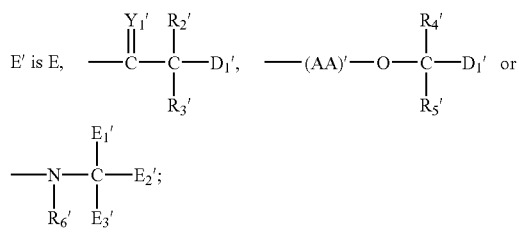

wherein:
$D_1'$ is a residue of a —SH containing moiety;
(AA)' is an amino acid residue;

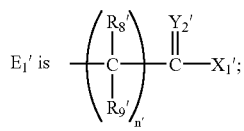

$E_2'$ and $E_3'$ are independently H, $E_1'$ or

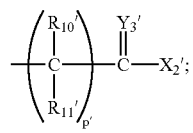

$Y_1'$, $Y_2'$ and $Y_3'$ are independently O, S or $NR_7'$;
$X_1'$ and $X_2'$ are independently OH or E;

$R_2'$, $R_3'$, $R_4'$, $R_5'$, $R_6'$, $R_7'$, $R_8'$, $R_9'$, $R_{10}'$ and $R_{11}'$ are independently selected from the group consisting of H, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and n' is zero or a positive integer; and
p' is zero or a positive integer.

In this aspect of the invention prodrugs corresponding to Formula II are provided:

$$E'\text{-}R_1\text{-}E \qquad (II)$$

wherein all variables are as previously described.

Within these aspects of the invention, n, n', p and p' preferably are independently zero, one or two, $R_2$, $R_2'$, $R_3$ and $R_3'$ are each H, all Y variables are O and both $E_1$ and $R_6$ are H.

B. Substantially Non-Antigenic Polymers

As stated above, $R_1$ is a water soluble polymeric residue which is preferably substantially non-antigenic such as a polyalkylene oxide or polyethylene glycol (PEG). In preferred aspects of the invention, $R_1$ further includes the previously mentioned capping group, designated herein as Z, which allows a bifunctional or bis polymer system to be formed.

As an example, the PEG residue portion of the inventive compositions can be selected from the following non-limiting list:

—C(=Y_4)—(CH_2)_t—O—(CH_2CH_2O)_x-A,
—C(=Y_4)—Y_5—(CH_2)_t—O—(CH_2CH_2O)_x-A,
—C(=Y_4)—NR_{14}—(CH_2)_t—O—(CH_2CH_2O)_x-A,
—(CR_{15}R_{16})_e—O—(CH_2)_t—O—(CH_2CH_2O)_x-A,
—NR_{14}—(CH_2)_t—O—(CH_2CH_2O)_x-A,
—C(=Y_4)—(CH_2)_t—O—(CH_2CH_2O)_x—(CH_2)_t—C(=Y_4)—,
—C(=Y_4)—Y_5—(CH_2)_t—O—(CH_2CH_2O)_x—(CH_2)_t—Y_5—C(=Y_4)—,
—C(=Y_4)—NR_{14}—(CH_2)_t—O—(CH_2CH_2O)_x—(CH_2)_t—NR_{14}—C(=Y_4)—,
—(CR_{15}R_{16})_e—O—(CH_2)_t—O—(CH_2CH_2O)_x—(CH_2)_t—O—(CR_{15}R_{16})_e—, and
—NR_{14}—(CH_2)_t—O—(CH_2CH_2O)_x—(CH_2)_t—NR_{14}— wherein:
x is the degree of polymerization;
$R_{14}$, $R_{15}$ and $R_{16}$ are independently selected from among H, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
e and t are independently zero, one or two;
$Y_4$ and $Y_5$ are independently O, S or $NR_{12}$; and
A is a capping group.

The degree of polymerization for the polymer can be from about 10 to about 2,300. This represents the number of repeating units in the polymer chain and is dependent on the molecular weight of the polymer. The (A) moiety is a capping group i.e., a group which is found on the terminal of the polymer, and can be selected from any of H, $NH_2$, OH, $CO_2H$, $C_{1-6}$ alkyls or other activating groups.

Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998". The disclosure of each of the foregoing is incorporated herein by reference. It will be understood that the water-soluble polymer can be functionalized for attachment to the bifunctional linkage groups if required without undue experimentation.

In a further embodiment $R_1$ is optionally selected from among one or more of dextran, polyvinyl alcohols, carbohydrate-based polymers, hydroxypropyl-methacryl-amide, polyalkylene oxides, and/or copolymers thereof. See also commonly-assigned U.S. Pat. No. 6,153,655, the contents of each are incorporated herein by reference.

In many aspects of the present invention, bis-activated polyethylene glycols are preferred when di- or more substituted polymer conjugates are desired. Alternatively, polyethylene glycols (PEG's), mono-activated, $C_{1-4}$ alkyl-terminated polyalkylene oxides (PAO's) such as mono-methyl-terminated polyethylene glycols (mPEG's) are preferred when mono-substituted polymers are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG-OH to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in average molecular weight, the polymer portion of the prodrug is at least about 20,000 weight average. Preferably, $R_1$ has a weight average molecular weight of from about 20,000 to about 100,000 and more preferably from about 25,000 to about 60,000. The average molecular weight of the polymer selected for inclusion in the prodrug must be sufficient so as to provide sufficient circulation of the prodrug before hydrolysis of the linker.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be clear from the foregoing that other polyalkylene oxide derivatives of the foregoing, such as the polypropylene glycol acids, etc., as well as other bi-functional linking groups are also contemplated.

C. Prodrug Candidates

As shown in Formulae (I) and (II), $D_1$ and $D_1'$ are independently selected residues of SH-containing moieties. A non-limiting list of suitable SH-containing moieties include biologically active materials such as 6-mercaptopurine, 6-thio-guanine or others as illustrated below:

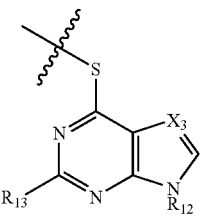

wherein
$R_{12}$ is one of H, a $C_{1-6}$ alkyl, alkoxy, or a carbohydrate of the formula:

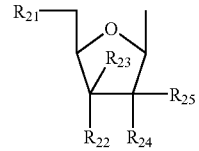

wherein $R_{21-25}$ are independently selected from alkoxy, e.g. $OR_{19}$ or, in the alternative, H, OH, $N_3$, $NHR_{20}$, $NO_2$ or CN, fluoro, chloro, bromo, jodo, where $R_{19-20}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, halo, substituted aryls, aralkyls, $C_{1-6}$ heteroalkyls, substituted $C_{1-6}$ heteroalkyls; and are preferably H or a $C_{1-4}$ alkyl;
$R_{13}$ is H or $NH_2$; and
$X_3$ is CH or N.
One preferred $R_{12}$ moiety is:

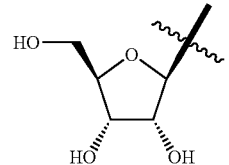

Other suitable candidates for inclusion in the prodrug systems described herein include biologically active compounds such as chemotherapeutic moieties containing a modifiable SH— group and/or polypeptides or enzymes, etc. containing modifiable cysteine residues. A non-limiting list of suitable biologically active compounds includes 1-β-D-arabinofuranosyl-thiopurine, penicillamine, 2-thiouracil, captopril, tiopronin, vasopressin, deaminooxytocin, thiopental sodium, etc.

D. Synthesis of Polymeric Prodrug Transport System

The prodrug conjugates of the present invention can be prepared in at least two ways, as well as by various permutations of the methods illustrated in the figures. Preferably, the thiol group of the biologically active compound of interest is modified to include the bifunctional linker and then this intermediate is reacted with an activated PEG or other similar polymer to form the conjugate. Alternatively, the activated polymer is reacted with the bifunctional linker and this intermediate is reacted with the thiol-containing biologically active composition of interest.

In those aspects of the invention where higher degrees of loading are required, the terminal branching of the polymer is done prior to attaching the thiol-bifunctional intermediate to allow 2, 3, 4, 6 or 8 equivalents of drug on each end of the polymer. Details concerning the formation of the terminal branching is provided in the examples and in commonly assigned U.S. Ser. No. 09/823,296, the contents of which are incorporated herein by reference.

Selection of a linker that will readily degrade in vivo is an important feature in determining the rate of hydrolysis in vivo. Such a linker is optionally built into either the activated functional group on the drug, or the activated functional group on the polymer, where it ultimately forms a degradable linker between the drug residue and the polymer residue in the prodrug conjugate.

Thus, in one preferred embodiment of the invention, the mercapto-drug of interest has at least one thiol functional group. The artisan will appreciate that certain mercapto drugs of interest will have two or more such thiol groups. FIG. 1 illustrates the reaction of 6-MP (1) with $BrCH_2CO_2$-t-Bu to form 6-MP t-Bu ester (2). Other suitable protecting groups useful for this purpose may be any of a variety of organic moieties known to those of ordinary skill in the art and include, without limitation, $CO_2H$ protecting groups, such as, for example, substituted silyl esters and substituted benzyl esters.

The intermediate is then deprotected, with a strong acid such as trifluoroacetic acid (TFA) or other haloacetic acid, HCl, sulfuric acid, etc., or by using catalytic hydrogenation. This leaves behind a thiol-linked reactive functional group, e.g., as illustrated by FIG. 1, compound (3), which includes a terminal carboxylic acid group. It will be appreciated that appropriate selection of the structure of the spacer group allows for substitution of any other art known reactive functional group, including an amine functional group, on the thiol.

Generally, it is convenient to use a system of conjugate formation wherein an acid derivative of the thiol containing drug reacts with an amine derivative of a desired polymer, or an amine derivative of the thiol containing drug reacts with an acid derivative of a desired polymer.

Preferably, a conjugate of an activated drug with a polymer, e.g., a suitable PAO, is formed by reacting the activated drug with any desired activated polymer, such as a mono or bis-activated PEG. As noted above, when drug intermediate is activated as an acid, the PAO is an activated PAO amine, as illustrated for PEG by FIG. 1, compound (4). The activated polymer can also include an activated acid group, e.g., a PAO acid, when the drug intermediate has an activated amine group. In either event, the resulting conjugate provides the compound of Formula I, as defined above and exemplified as (5).

Regardless of the methods employed, some preferred prodrugs are shown below:

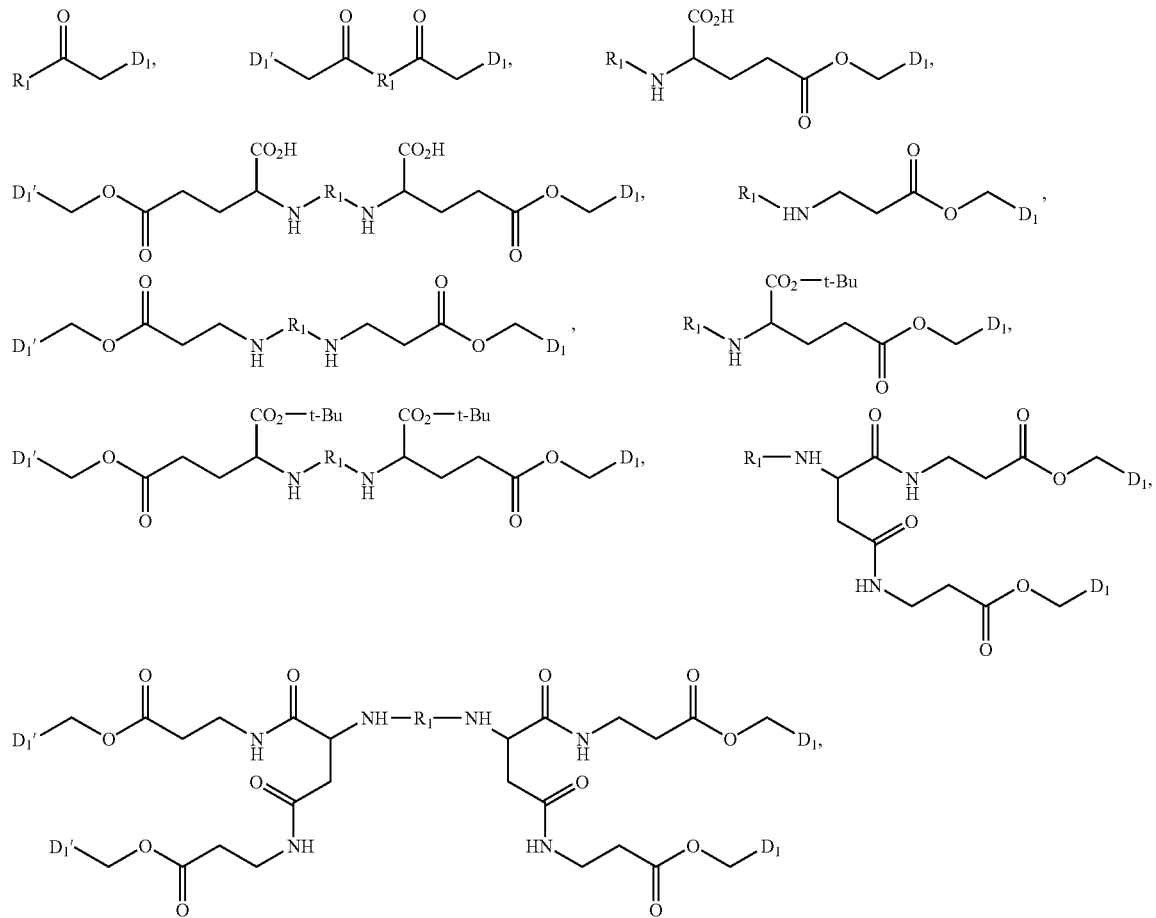

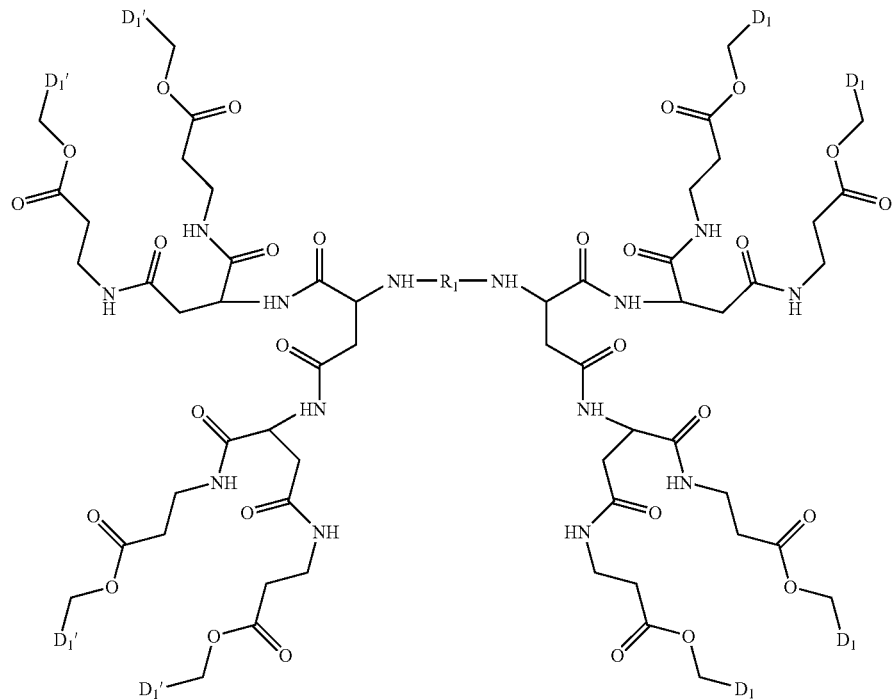
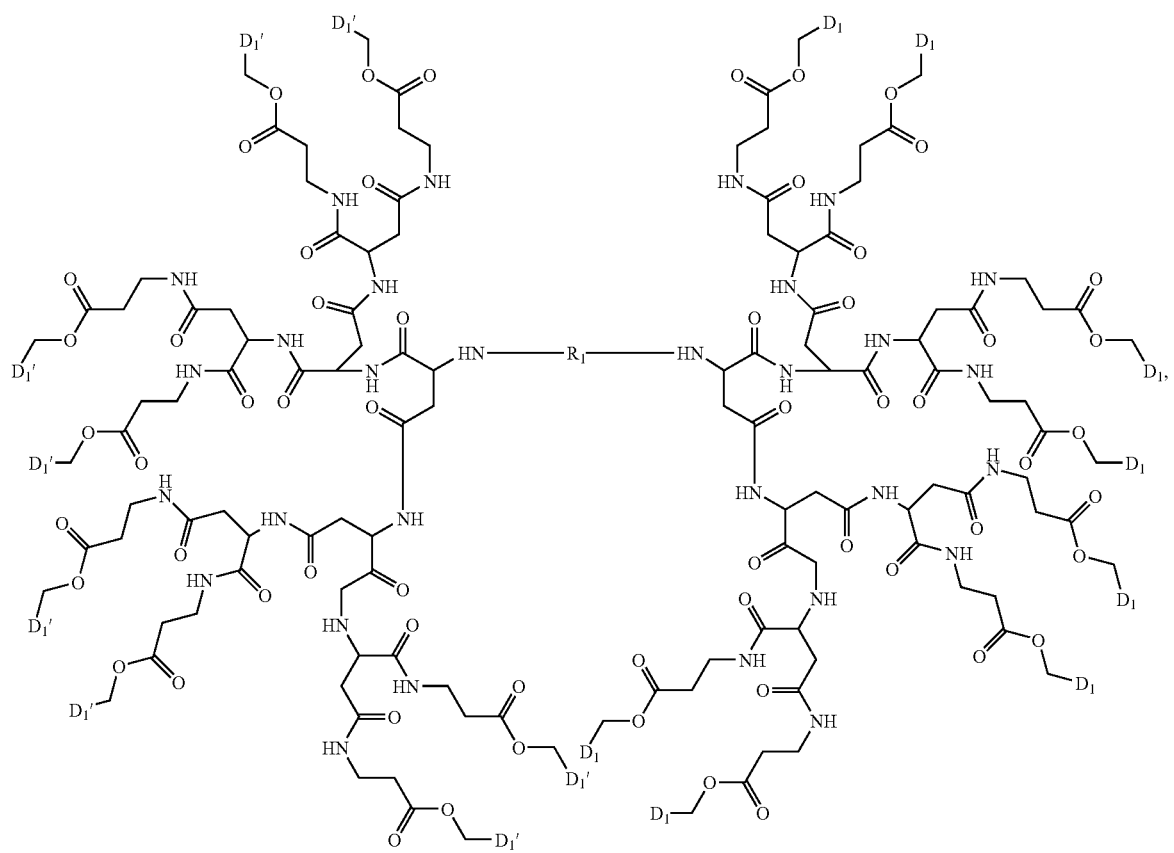

-continued
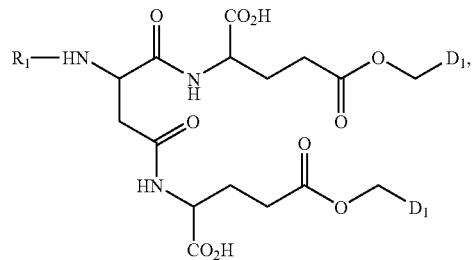
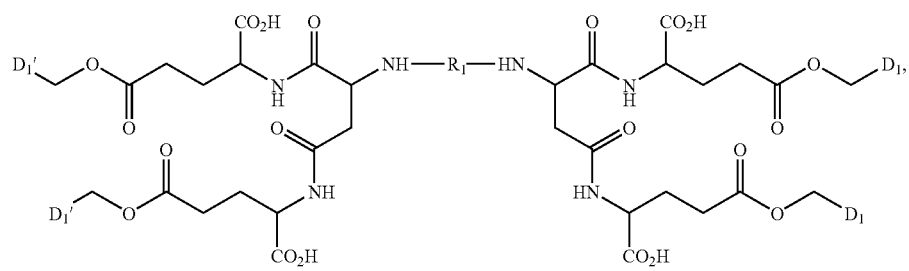
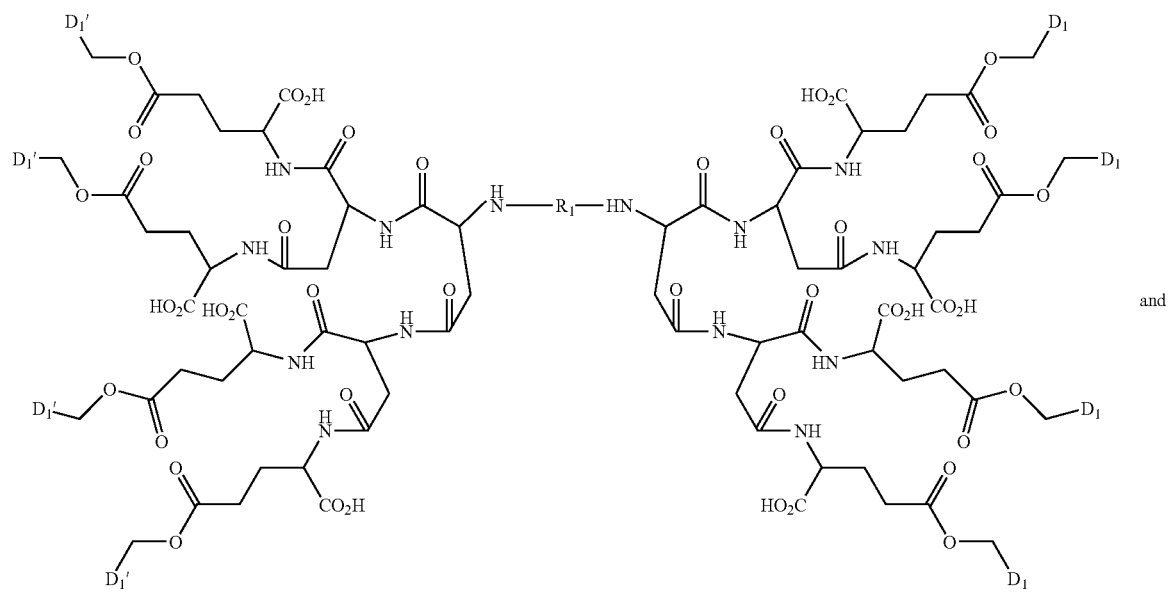
and

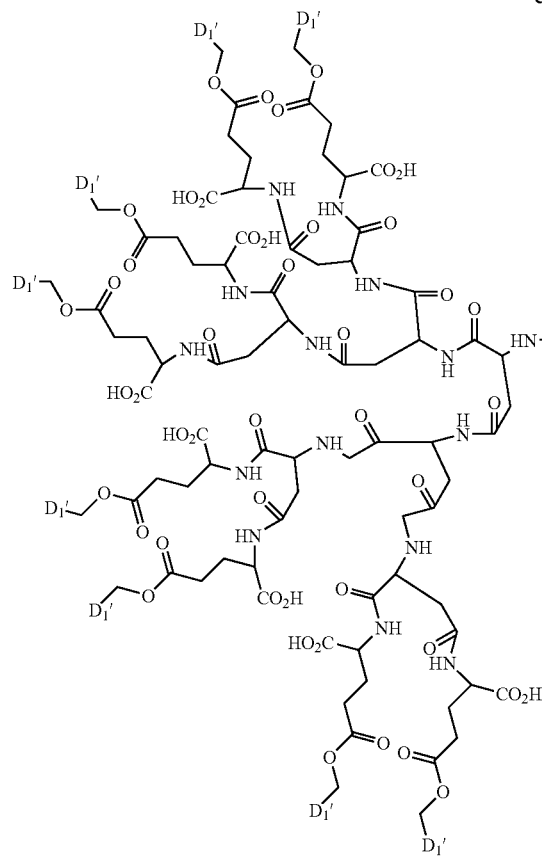
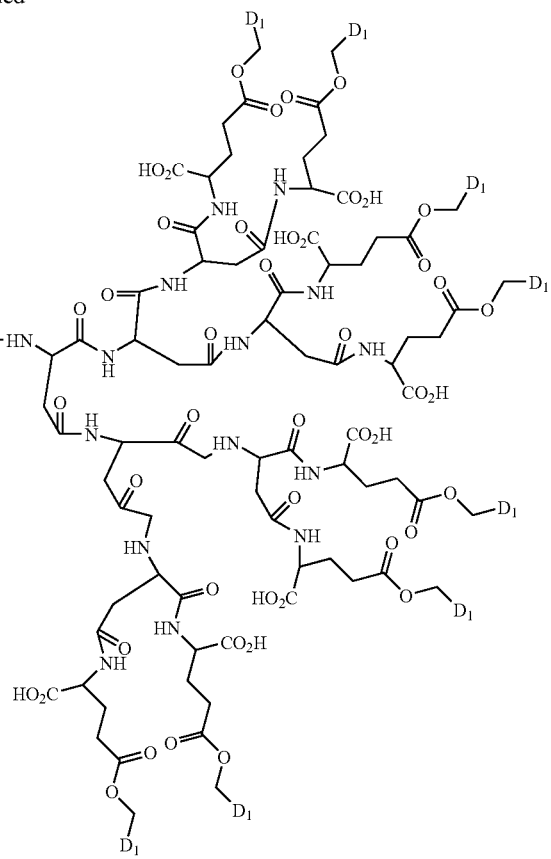

wherein:

$R_1$ is a straight or branched residue of a water soluble polymer and $D_1$ and $D_1'$ are residues of a —SH containing moiety which is preferably biologically active.

E. Methods of Treatment

Yet another aspect of the present invention provides methods of treatment for various medical conditions in mammals. The artisan will readily appreciate that the prodrugs of the invention are employed to treat diseases or disorders, or applied for diagnostic purposes that are the same or similar to the uses of the unmodified biologically effective compound.

The methods include administering to the mammal in need of such treatment, an effective amount of a prodrug, such as a 6-mercaptopurine PEG conjugate, which has been prepared as described herein. The compositions are useful for, among other things, treating neoplastic disease, reducing tumor burden, preventing metastasis of neoplasms, preventing recurrences of tumor/neoplastic growths in mammals. Further, a 6-mercaptopurine PEG conjugate has utility in modulating abnormal cell growth generally, and in particular, in treating and/or modulating autoimmune diseases and disorders, such as multiple sclerosis, and many other such art-known conditions.

The amount of the prodrug administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug a 6-mercaptopurine PEG conjugate are administered in amounts ranging from about 10 to about 30 mg/kg per day, based on the molar proportion of the 6-mercaptopurine moiety per mg of prodrug.

The range set forth above is illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are administered to mammals in need thereof by various art-known parenteral routes.

To the extent that 6-mercaptopurine has been exemplified herein, it is mentioned that polymer conjugates of 6-MP according to the invention are readily employed to treat the same range of diseases or disorders for which unmodified 6-MP and/or the previously known prodrug of 6-MP, azathioprine, which have been previously known to have some utility or potential.

F. Drug Generation via Hydrolysis of the Prodrug

The prodrug compounds of the present invention are designed so that the $t_{1/2}$ of hydrolysis is less than the $t_{1/2}$ of elimination in plasma. The linkages included in the compounds have in-vivo hydrolysis rates, in plasma, that are short enough to allow sufficient amounts of the transport enhanced conjugate with parent compounds, i.e., the amino- or hydroxyl-containing biologically active compound, to be released prior to elimination. Some preferred compounds of the present invention, i.e., those in which (n) and (n') of Formulae (I) and (II) are both 1, have a $t_{1/2}$ for hydrolysis in plasma ranging from about 5 minutes to about 12 hours. Preferably, the compositions have a plasma $t_{1/2}$ of hydrolysis ranging from about 0.5 to about 8 hours and most preferably from about 1 to about 6 hours.

G. EXAMPLES

The following non-limiting examples illustrate certain aspects of the invention. All parts and percentages are by weight unless otherwise noted and all temperatures are in degrees Celsius.

General Experimental

Materials and Methods. All reactions were run under an atmosphere of dry nitrogen or argon. Commercial reagents were used without further purification. All PEG compounds were dried under vacuum or by azeotropic distillation (toluene) prior to use. $^1$H spectra were obtained with a Varian MercuryVX-300 instrument using deuteriochloroform as solvent unless specified. $^{13}$C NMR spectra were obtained at 75.46 MHz on the Varian MercuryVX-300. Chemical shifts (δ) are reported in parts per million (ppm) downfield from tetramethylsilane (TMS) and coupling constants (J values) are given in hertz (Hz).

HPLC Method. Analytical HPLC's were performed using a size exclusion column (PolySep-GFC-P3000, Phenomenex) under isocratic conditions with a 1:1 mixture (v/v) of methanol-water as mobile phase. Peak elution was monitored at 254 nm using a UV detector. To detect the presence of any free PEG and also to confirm the presence of PEGylated product, an evaporative light scattering detector (ELSD), Model 5000 ELSD (Alltech), was employed. Based on ELSD and UV analysis, all the final PEGylated products were free of native drug and were ≧95% pure by HPLC.

Analysis of 6-mercaptopurine Content in PEG Derivatives. For the determination of the 6-mercaptopurine content in PEG derivatives, the UV absorbance of 6-mercaptopurine in 90% MeOH in H$_2$O (v/v) was determined at 277 nm for five different concentrations ranging from 0.02 μmol/mL to 0.10 μmol/mL. From the standard plot of absorbance vs. concentration, the absorption coefficient, ε, of 6-mercaptopurine was calculated to be 21.6 (O.D. at 277 nm for 1 mg/mL with 1.0 cm light path). PEGylated 6-mercaptopurine derivatives were dissolved in 90% MeOH in H$_2$O (v/v) at an approximate concentration of 0.006 μmol/mL (based on a MW of 40,000) and the UV absorbance of these compounds at 277 nm was determined. Using this value and employing the absorption coefficient, ε, obtained from the above, the concentration of 6-mercaptopurine in the sample was determined. Dividing this value by the sample concentration provided the percentage of 6-mercaptopurine in the sample.

Determination of Rates of Hydrolysis of PEG Prodrugs. The rates of hydrolysis were obtained by employing a C8 reversed phase column (Zorbax® SB-C8) using a gradient mobile phase consisting of (a) 0.1 M triethylammonium acetate buffer and (b) acetonitrile. A flow rate of 1 mL/min was used, and chromatograms were monitored using a UV detector at 254 nm for 6-mercaptopurine. For hydrolysis in plasma, the derivatives were dissolved in acetonitrile at a concentration of 20 mg/mL. The solution was divided into vials with 100 μL and the solvent removed in vacuo. To the residue, 100 μL of plasma was added, then the mixture was vortexed for 10 seconds. The solutions were incubated at 37° C. for various periods of time. A mixture of methanol-acetonitrile (1:1, v/v, 400 μL) was added to a vial at the proper interval and the mixture was vortexed for 1 minute, followed by filtration through 0.45 μm filter membrane (optionally followed by a second filtration through 0.2 μm filter membrane). An aliquot of 40 μL of the filtrate was injected into the HPLC. On the basis of the peak area, the amounts of native compound and PEG derivative were estimated, and the half-life of each compound in different media was calculated using linear regression analysis from the disappearance of PEG derivative.

Abbreviations. DCM (dichloromethane), DMAP (4-(dimethylamino)pyridine), DMF (N,N-dimethylformamide), EDC (1-ethyl-3-(3-dimethylaminopropyl)carbodiimide), IPA (2-propanol), TFA (trifluoroacetic acid).

Example 1

Preparation of Spacer-6-MP t-Bu ester (2)

A solution of t-butyl bromoacetate (441 mg, 2.26 mmol) in anhydrous DMF (0.5 mL) was added to a stirred mixture of 6-mercaptopurine monohydrate (1, 340 mg, 2 mmol) in DMF (2.0 mL) dropwise. The reaction mixture was stirred at room temperature for 0.5 hours. Water (25 mL) was added to precipitate a white solid, which was filtered, washed with water, dried, and followed by purification by silica gel column chromatography (40% EtOAc in hexane, v/v) to give 260 mg (49%) of product (2) as a white solid: $^1$H NMR δ 1.50 (s, 9H, t-Bu), 1.65 (bs, NH), 4.11 (s, 2H, SCH$_2$CO$_2$), 8.16 (s, 1H, Ar—H), 8.72 (s, 1H, Ar—h); $^{13}$C NMR δ 27.98, 32.32, 82.44, 141.11, 148.89, 151.41, 151.91, 168.13.

Example 2

Preparation of Spacer-6-MP (3)

TFA (1 mL) was added to a suspension of (2) (120 mg, 0.45 mmol) in DCM (2 mL) and the mixture was stirred for 4 h at room temperature. The solvent was removed in vacuo and EtOAc (0.5 mL) and ether (10 mL) were added to precipitate the solid, which was filtered and washed with ether to give the desired product (3) (94 mg, 99%): $^1$H NMR (DMSO-d$_6$) δ 4.18 (s, 2H, SCH$_2$CO$_2$), 8.47 (s, 1H, Ar—H), 8.67 (s, 1H, Ar—H).

Example 3

Preparation of PEG-spacer-6-MP (5)

A mixture of (3) (22.4 mg, 0.1 mmol), PEG diamine HCl (4, mw. 40,000, 1.0 g, 0.025 mmol), EDC.HCl (28.8 mg, 0.15 mmol) and DMAP (36.6 mg, 0.3 mmol) in anhydrous DMF (5 mL) and DCM (15 mL) was stirred at room temperature overnight. The solvent was removed in vacuo and the residue recrystallized twice from IPA to give 0.9 g (90%) of product (5). The content of (1) in the compound measured by UV assay was 0.75% wt/wt: $^{13}$C NMR δ 32.050, 39.437, 61.586, 130.601, 142.961, 151.767, 158.382, 168.971.

Example 4

Preparation of Boc-Glu-(O-t-Bu)(OCH$_2$Cl) (7)

A mixture of Boc-Glu-O-t-Bu (6, 9.58 g, 30 mmol), K$_2$CO$_3$ (4.15 g, 30 mmol), NaI (4.5 g, 30 mmol), and ClCH$_2$Br (7, 20 mL, 307.76 mmol) was stirred at room temperature for 3 days, followed by filtration through a celite pad and a short silica gel column washed with EtOAc. The filtrate was concentrated in vacuo to give 4.0 g (38%) of product (7): $^{13}$C NMR δ 28.020, 28.327, 30.157, 53.287, 68.814, 80.232, 82.600, 155.635, 155.919, 171.523, 177.321.

Example 5

Preparation of Boc-Glu(O-t-Bu)-6-MP (8)

A suspension of 7 (4.0 g, 10.8 mmol) and NaI (1.62 g, 10.8 mmol) in acetone (20 mL) was stirred for 1 hour at room temperature, followed by addition of a solution of (1) (1.7 g, 10.0 mmol) and K$_2$CO$_3$ (1.38 g, 10.0 mmol) in DMF (20 mL). The mixture was stirred at room temperature overnight, followed by filtration. The filtrate was concentrated in vacuo and the residue dissolved in EtOAc (200 mL), washed with water (200 mL), brine (100 mL), and dried over anhydrous MgSO$_4$. The solvent was removed in vacuo and the residue purified by silica gel column chromatography (10% MeOH in CHCl$_3$, v/v) to give 1.1 g (23.5%) of product (8): $^{13}$C NMR (CDCl$_3$+CD$_3$OD) δ 26.439, 26.759, 29.883, 35.643, 52.859, 60.091, 81.237, 81.339, 142.703, 151.266, 155.887, 162.902, 171.132, 171.503, 172.220, 175.792.

Example 6

Preparation of 6-MPG TFA salt (9)

A solution of (8) (1.0 g, 2.06 mmol) in DCM (5 mL) and TFA (5 mL) was stirred for 2 h at room temperature. The solvent was removed and the residue triturated with hexane to remove TFA. The material was dried at 40° C. in vacuo to give 620 mg (63%) of product (9) $^1$H NMR data confirmed the completion of the reaction.

Example 7

Preparation of PEG-6-MPG (11)

A mixture of BSC-PEG (10, 5.0 g, 0.125 mmol), (9) (120 mg, 0.375 mmol), and DMAP (91.5 mg, 0.75 mmol) in anhydrous CHCl$_3$ (50 mL) was refluxed overnight. Ethyl ether (250 mL) was added to precipitate the solid, which was recrystallized from IPA to give 4.3 g (96%) of product (11). The content of 1 in the compound measured by UV assay was 0.39% wt/wt.

Example 8

Boc-β-Ala-CH$_2$Cl (13)

A mixture of ICISO$_3$H (5 g, 42.91 mmol) and ClCH$_2$Br (5.55 g, 42.9 mmol) was refluxed for 3 hours, followed by pouring into ice. The ice water suspension was extracted with DCM (2×50 mL), and the combined DCM layers were washed with water (2×50 mL) to give a solution of ClCH$_2$SO$_3$Cl (solution A). A solution of Boc-β-Ala-OH (12, 4.73 g, 25 mmol), NaHCO$_3$ (8.41 g, 100 mmol), and Bu$_4$N$^+$HSO$_4^-$ (0.849 g, 2.5 mmol) in water (100 mL) was cooled to 0° C., followed by addition of solution A. The mixture was stirred vigorously for 2 hours, followed by separation of the layers. The DCM layer was washed with brine (2×100 mL), and dried over anhydrous MgSO$_4$. The solvent was removed in vacuo and the residue purified by silica gel column chromatography (20% EtOAc in hexane, v/v) to yield 1.2 g (20%) of product (13): $^{13}$C NMR δ 28.218 (3×CH$_3$ of Boc), 34.439 (CH$_2$C(=O)O), 35.655 (NHCH$_2$CH$_2$), 68.565 (OCH$_2$Cl), 79.547 (C(CH$_3$)$_3$), 155.811 (NHC(=O)O), 170.761 (C(=O)O).

Example 9

Preparation of Boc-β-Ala-6-MP (14)

A suspension of (13) (1.0 g, 4.2 mmol) and NaI (0.755 g, 5.04 mmol) in acetone (15 mL) was stirred for 1 hour at room temperature, followed by addition of a solution of (1) (0.595 g, 3.5 mmol) and CaCO$_3$ (1.738 g, 17.4 mmol) in DMF (15 mL). The mixture was stirred at room temperature overnight, followed by filtration. The filtrate was concentrated in vacuo and the residue dissolved in EtOAc (100 mL), washed with water (100 mL), brine (100 mL), and dried over anhydrous MgSO$_4$. The solvent was removed in vacuo and the residue purified by silica gel column chromatography (0 to 5% MeOH in CHCl$_3$, v/v) to give 340 mg (28.6%) of product (14): $^{13}$C NMR (CDCl$_3$+CD$_3$OD) δ 28.429 (3×CH$_3$ of Boc), 34.868 (CH$_2$C(=O)O), 36.109 (NHCH$_2$CH$_2$), 61.223 (OCH$_2$S), 81.537 (C(CH$_3$)$_3$), 142.901 (Ar—C), 145.640 (Ar—C), 148.623 (Ar—C), 149.749 (Ar—C), 152.181 (Ar—C), 156.738 (NHC(=O)O), 172.431 (C(=O)O).

Example 10

Preparation of β-Ala-6-MP TFA salt (15)

A solution of (14) (140 mg, 0.4 mmol) in DCM (1 mL) and TFA (1 mL) was stirred for 2 hours at room temperature. The solvent was removed and the residue was triturated with hexane to remove TFA. The material was dried at 40° C. in vacuo to give 170 mg (100%) of product (15). $^1$H NMR data confirmed the completion of reaction.

Example 11

Preparation of PEG-cmc-Asp-O-t-Bu (17)

Compound (10) (40,000, 20 g, 0.459 mmol) and aspartic acid di t-butyl ester HCl (1.0 g, 3.55 mmol) were dissolved in anhydrous DCM, followed by addition of DMAP (0.433 g, 3.55 mmol). The solution was refluxed overnight followed by precipitation by addition of ethyl ether (1 L). The solid was isolated by filtration and recrystallized from IPA (1 L) twice. The filter cake was washed with IPA (200 mL) and ether (200 mL) to give 15.6 g (78%) of product (17) after drying at 45° C. in vacuo: $^{13}$C NMR δ 27.837 ($CH_2CO_2C(CH_3)_3$), 27.991 ($CHCO_2C(CH_3)_3$), 37.752 ($CH(CH_2CO_2)$), 50.800 (NHCH), 64.212 ($OCH_2CH_2OC(=O)NH$), 81.333 ($CH_2CO_2C(CH_3)_3$), 82.007 ($CHCO_2C(CH_3)_3$), 155.924 ($OCH_2CH_2OC(=O)NH$), 169.674 ($CH_2CO_2C(CH_3)_3$), 169.969 ($CHCO_2C(CH_3)_3$).

Example 12

Preparation of PEG-cmc-Asp-OH (18)

Compound (17) (15 g, 0.375 mmol) was dissolved in DCM (150 mL) followed by addition TFA (75 mL). The solution was stirred at room temperature for 2 h and hexane (500 mL) added to precipitate the solid. The solid was triturated with hexane to remove TFA followed by recrystallization from chilled DCM-ether. The recrystallized solid was redissolved in DCM (150 mL) and washed with water (150 mL). The organic layer was separated, dried over anhydrous $MgSO_4$, concentrated in vacuo, and precipitated with ether to give 12.4 g (83%) of product (18): $^{13}$C NMR δ 36.441 ($CHCH_2CO_2$), 50.177 (NHCH), 64.390 ($OCH_2CH_2OC(=O)NH$), 81.333 ($CH_2CO_2C(CH_3)_3$), 82.007 ($CHCO_2C(CH_3)_3$), 156.172 ($OCH_2CH_2OC(=O)NH$), 171.944 ($CH_2CO_2C(CH_3)_3$), 172.211 ($CHCO_2C(CH_3)_3$).

Example 13

Preparation of Compound 19

Compound (15) (160 mg, 0.436 mmol) was dissolved in DMF (5 mL), followed by addition of DCM (25 mL), (18) (3.0 g, 0.075 mmol), and DMAP (212 mg, 1.744 mmol). The solution was cooled to 0° C., and EDC.HCl (167 mg, 0.872 mmol) added to the solution. The mixture was stirred at 0° C. to room temperature overnight, concentrated in vacuo, and the crude product was precipitated by addition of ether. The solid was recrystallized from IPA twice to give 2.7 g (90%) of product (9). The content of (1) in the compound measured by UV assay was 1.47% wt/wt.: $^{13}$C NMR ($CDCl_3+CD_3OD$) δ 33.777 & 33.876 ($CH_2C(=O)O$), 34.887 & 35.013 ($NHCH_2CH_2$), 37.738 (Asp's $CH_2C(=O)NH$), 51.628 (Asp's NHCH), 60.898 ($OCH_2S$), 64.381 (PEG's $CH_2OC(=O)NH$), 143.087 (Ar—C), 145.699 (Ar—C), 148.958 (Ar—C), 151.879 (Ar—C), 156.219 (NHC(=O)O), 170.839, 171.373, 171.710, 171.893 (C(=O)O & C(=O)NH).

Example 14

PEG acid 4-amino-4-(2-tert-butoxycarbonyl-ethyl)-heptanedioic acid di-tert-butyl ester amide (22)

A mixture of PEG 40,000 diacid (21) (5.0 g, 0.125 mmol), 4-amino-4-(2-tert-butoxycarbonylethyl)-heptanedioic acid di-tert-butyl ester (20) (310 8 mg, 0.75 mmol), EDC.HCl (143.6 mg, 0.75 mmol), and DMAP (252 mg, 2.25 mmol) in anhydrous DCM is stirred at room temperature overnight. The reaction solution is concentrated in vacuo and the residue recrystallized from IPA to give the product (22).

Example 15

PEG acid 4-amino-4-(2-carboxyethyl)-heptanedioic acid amide (23)

Compound (22) (4.0 g, 0.1 mmol) is stirred in 25 mL of TFA and 50 mL of anhydrous DCM at room temperature for 5 hours. The solvent is removed in vacuo followed by recrystallization of the residue from chilled DCM/ether (20% v/v DCM in ether, total ca. 100 mL). The wet solid is redissolved in $H_2O$ (20 mL) and the solution is stirred for 30 minutes at room temperature, followed by extraction with DCM (60 mL). The organic layer is dried over anhydrous $MgSO_4$ and the solvent is removed in vacuo followed by crystallization with DCM/ether to give the product (23).

Example 16

Hexamer-loaded PEG-spacer-Drug Derivative (24)

EDC.HCl (571.1 mg, 2.97 mmol) is added to a mixture of (23) (5.0 g, 0.124 mmol), (15) (682.6 mg, 1.86 mmol), NMM (600 mg, 5.96 mmol), and HOBT (302 mg, 2.24 mmol) in anhydrous DCM (80 mL) and DMF (50 mL) at 0° C. and the mixture is slowly warmed to room temperature overnight. The solvent is removed and the residue recrystallized from IPA to give (24).

Example 17

Compound (27)

EDC.HCl (2.47 g, 12.86 mmol) was added to a mixture of BocNH-aspartic acid (25, 1 g, 4.29 mmol), aspartic acid dimethyl ester HCl (26, 1.86 g, 9.43 mmol), and DMAP (2.47 g, 12.86 mmol) in anhydrous DCM (30 mL) and DMF (2 mL) at 0° C. and the mixture was stirred at 0° C. to room temperature overnight. The mixture was washed with 1N HCl three times and the organic layer was dried over anhydrous $MgSO_4$, followed by removal of the solvent in vacuo to give the product (27) (2.0 g, 90%): $^1$H NMR δ 1.45 (s, 9H), 2.62–3.02 (m, 6H, 3×CH), 3.70 (s, 6H, 2×$OCH_3$), 3.74 (s, 3H, $OCH_3$), 3.75 (s, 3H, $OCH_3$), 4.50 (bs, 1H, CH), 4.85 (m, 2H, 2×CH), 6.05 (d, J=6.95, 1H, NH), 6.98 (d, J=8.05, 1H, NH), 7.57 (d, J=7.69, 1H, NH); $^{13}$C NMR, δ 28.178, 31.315, 35.846, 36.384, 37.223, 48.434, 48.619, 50.952, 51.908, 51.976, 52.697, 80.139, 162.462, 170.569, 170.804, 170.871, 170.972, 171.291.

Example 18

Compound (28)

Compound (27) (2.0 g, 3.85 mmol) was dissolved in DCM (30 mL) and TFA (15 mL) and the solution was stirred for 2 hours at room temperature. The solvent was removed in vacuo and the residue was recrystallized twice with DCM-ether to give the product (28) (1.74 g, 87%) as a white solid: $^{13}$C NMR δ 35.52, 48.76, 50.12, 51.90, 51.96, 52.65, 114.59, 118.49, 168.43, 170.02, 170.92, 171.17, 171.40, 171.48.

Example 19

Compound (29)

EDC.HCl (191.4 mg, 1.00 mmol) was added to a mixture of PEG-acid 40,000 (21, 5.0 g, 0.12 mmol), (28) (209 mg, 0.50 mmol), DMAP (212.9 mg, 1.75 mmol) in anhydrous DCM (80 mL) at 0° C. and the mixture was stirred at 0° C. to room temperature overnight. The solvent was removed in vacuo and the residue was recrystallized from IPA to give product (29) (4.5 g, 90%): $^{13}$C NMR δ 35.43, 36.71, 48.15, 48.25, 48.70, 51.50, 52.18, 52.24, 69.96–70.58 (PEG), 169.77, 169.82, 170.29, 170.40, 170.69.

Example 20

Compound (30)

Compound (29) (4.5 g, 0.11 mmol) and LiOH.H$_2$O (71.6 mg) was stirred in water (25 mL) overnight at room temperature. pH was adjusted to 2.5 by addition of 1N HCl followed by extraction of the product into DCM three times. The organic layer was dried over anhydrous MgSO$_4$ and the solvent was removed in vacuo. The residue was recrystallized from IPA to give the product (30) (3.6 g, 80%): $^{13}$C NMR (D$_2$O) δ 39.59, 40.65, 52.74, 54.31, 71.85–74.40 (PEG), 173.73, 173.92, 175.07, 178.99, 179.24, 179.35, 179.62.

Example 21

Octamer Loaded PEG Spacer-Drug Derivative (31)

EDC.HCl (391 mg, 2.04 mmol) is added to a mixture of (30) (2.6 g, 0.06 mmol), 15 (466.1 mg, 1.27 mmol), HOBT (206.2 mg, 1.53 mmol), and NMM (411.3 mg, 4.07 mmol) in anhydrous DCM (40 mL) and DMF (25 mL) at 0° C. and the mixture is stirred at 0° C. to room temperature overnight. The solvent is removed in vacuo and the residue is recrystallized from IPA to give product (31).

Example 22

Compound (32)

Compound (27) (100 mg, 0.11 mmol) and LiOH H$_2$O (71.6 mg) is stirred in water (25 mL) overnight at room temperature. pH is adjusted to 2.5 by addition of 1N HCl followed by extraction of the product into DCM three times. The organic layer is dried over anhydrous MgSO$_4$ and the solvent is removed in vacuo to give the product (32).

Example 23

Compound (35)

Compound (35) is prepared using the conditions in Examples 17–21 from (32) instead of (25).

Example 24

In vitro Experiment

Cell Lines and Cytotoxicity Assays. Studies using P388/0 cell lines for IC$_{50}$ (drug concentration inhibiting growth of cells by 50%) were maintained and conducted as previously reported. Briefly, for IC$_{50}$ determination, cells were seeded into the microwell plates at a density of 2×10$^3$ cells per 50 µL per well. Plates were incubated at 37° C. in a humidified incubator with 5% CO$_2$ for 3 days. Cell growth was measured by the addition of 10 µL/well of Alamar Blue (Alamar Biosciences, Inc., Sacramento, Calif.) and the plates were incubated a further 4 h at 37° C. The IC$_{50}$ values for each compound were determined from absorbance versus dilution factor plots. All cell cultures for animal implantation were maintained at 37° C. in a humidified atmosphere of 5% CO$_2$/95% O$_2$ and subcultured once a week. All cell lines were periodically tested for Mycoplasma and were Mycoplasma free. The results are shown in Table 2.

TABLE 1

In vitro results of 6-MP and Its PEG Derivatives.

| Compound | $t_{1/2}$ in PBS, pH 7.4 | $t_{1/2}$ in rat plasma at 37° C. | $t_{1/2}$ in human plasma at 37° C. | IC$_{50}$ (P388/0, µM) |
|---|---|---|---|---|
| 6-MP(1) | — | — | — | 2.67 |
| 5 | >24 h | 43 h | 112 h | no inhibition |
| 11 | >24 h | 7.3 h | 10 h | no inhibition |
| 19 | >24 h | 1.1 h | 2.7 h | no inhibition |

The indication of no inhibition shows that the prodrug is substantially inactive until the parent molecule is released from the polymer transport.

Example 25

In vivo Experiment

M109 cells (NCI), derived from donor mice, were grown and expanded in tissue culture for in vivo implantation. Cells were grown in EMEM with 10% FBS and 1% streptomycin/penicillin media, kept in an incubator at 37° C. with 5% CO$_2$ and split twice a week. Cells were trypsinized, harvested, washed, counted and prepared in PBS for transport to the vivarium. Cells were kept on ice until implantation was conducted with minimum lag time. A cell suspension of approximately 5×10$^6$ cells/mL was used. Balb/C mice were implanted subcutaneous with 100 µL of the above cell suspension (Day 0). Treatments were administered intravenously on Day 1 and Day 4. Compound doses were based on the content of 6-MP. Body weight and tumor volume were then measured twice weekly until the group's median tumor volume exceeded 2000 mm$^3$. The tumor volume for each mouse was determined by measuring two dimensions with calipers and calculated using the formula: tumor volume= (length×width$^2$)/2. Drug effects were determined by comparing tumor growth in treated versus control (no vehicle) mice. Three types of endpoints were used as the basis for comparison: (a) the percent difference in tumor volume (% T/C), measured when the control group's median tumor volume reached approximately 800–1100 mm$^3$ (exponential growth phase), (b) again when the control group's median tumor volume was approximately 2000 mm$^3$ and (c) the number of tumor regression (smaller tumor volume on Day 25 compared to Day 1) per group.

Results

Unmodified 6-MP was ineffective at inhibiting the growth of M109 solid tumors. In contrast, PEG-6-MP conjugates caused roughly a 25 to 35% reduction in tumor growth as compared to control (Table 1).

TABLE 2

Efficacy Comparison Between 6-MP And PEG-MP $^\alpha$ Against Lung M109 Syngeneic Solid Tumors In Balb/C Mice.

| Compound | Total Dose (mg/kg) | T/C (%)$^x$ at Day 18 | T/C (%)$^x$ at Day 25 |
|---|---|---|---|
| Control | 0 | — | — |
| 1 | 60 | 127.1 | 122.0 |
| 1 | 200 | 144.0 | 183.8 |
| 5 | 30 | 99.0 | 73.2 |
| 11 | 20 | 102.1 | 67.6 |
| 19 | 60 | 122.0 | 65.7 |

$^\alpha$ All PEG compounds were given clay 1 & 4, i.v.
$^x$The median tumor volume of treatment and control groups were measured and compared when the control group's median tumor volume reached approximately 1000 mm$^3$ (day 18) and 2000 mm$^3$ (day 25).

Example 26

In vivo Experiment with L1210 Tumor Model

6-MP and pro-drug forms of 6-MP were screened for in vivo activity against the murine leukemia cell line L1210/O (mouse, lymphocytic leukemia). The cell line was obtained from Southern Research Institute (Birmingham, Ala.) and grown in DMEM supplemented with 10% horse serum. L1210/O cells were subcultured two times per week and log phase cultures (viability≧95%) were used for all in vivo experiments. Female CD2F1 mice (Taconic Farms, Germantown, N.Y.) at 7–8 weeks of age were used for study. Following one week of acclimation, mice were implanted i.p. with L1210/O cells (5×10$^5$ cells/mouse) at designated day 0. The mice were randomly assigned to experimental groups (8–10/group). The groups included control, 6-MP and PEG-6-MP conjugates. 6-MP was solubilized in 3% DMSO and suspended in intralipid and administered Q2d×6, IP. PEG-6-MP was dissolved in phosphate buffer (pH 5.8) and administered Q4d×3, IV. Control groups received vehicle (intralipid or phosphate buffer). The mice were monitored for up to 40 days, and the treatment was evaluated as percentage of increase in life span (ILS).

Results

The PEG-6-MP conjugate (19) showed significantly (P<0.05) greater survival in this ascites model (Table 3) than both vehicle control and the 6-MP matched dose equivalent.

TABLE 3

Efficacy Comparison of PEG-6MP Analog Against a Murine Leukemia (L1210/0) Ascites Model

| Compound | Total Dose (mg/kg) | % ILS$^a$ |
|---|---|---|
| 1 | 90 | 31.8 |
|   | 240 | 52.5* |
| 19 | 90 | 84.1*+ |

$^a$Percent increase in life span (% ILS) was calculated from the quotient of the treatment group mean survival divided by the control group mean survival [(T/C-1) × 100].
*Significant (P < 0.05) vs. untreated control group.
$^+$ Significant (P < 0.05) vs. 6-MP matched treatment.

The invention claimed is:

1. A prodrug compound comprising the formula: (I) R$_1$-E that releases an —SH-containing biologically active moiety wherein:

R$_1$ is a straight or branched residue of a water soluble polymer;

E is 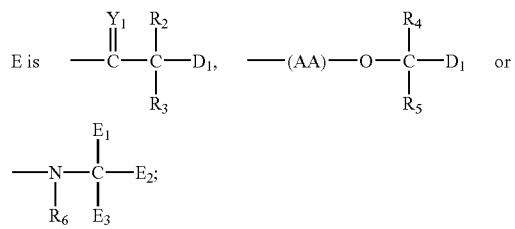

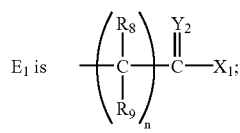

wherein:

D$_1$ is a residue of an —SH-containing biologically active moiety bonded through the sulfur;

(AA) is an amino acid residue;

E$_1$ is 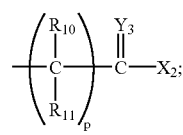

E$_2$ and E$_3$ are independently H, E$_1$ or

Y$_1$, Y$_2$ and Y$_3$ are independently O, S or NR$_7$;

X$_1$ and X$_2$ are independently OH or E;

R$_2$, R$_3$, R$_4$, R$_5$, R$_6$, R$_7$, R$_8$, R$_9$, R$_{10}$ and R$_{11}$ are independently selected from the group consisting of H, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy;

n is zero or a positive integer; and p is zero or a positive integer.

2. The compound of claim 1, wherein R$_1$ further comprises a capping group selected from the group consisting of hydrogen, NH$_2$, OH, CO$_2$H, C$_{1-6}$ moieties and

E'-         (I')

wherein:

E' is E, 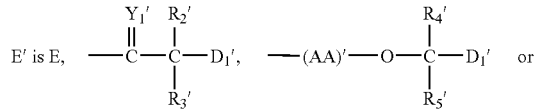

-continued

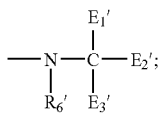

wherein:
$D_1'$ is a residue of an —SH-containing biologically active moiety bonded through the sulfur;
(AA) is an amino acid residue;

$E_1'$ is 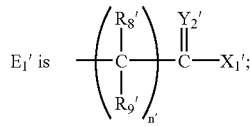

$E_2'$ and $E_3'$ are independently H, $E_1'$ or

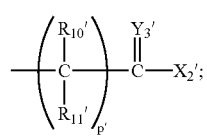

$Y_1'$, $Y_2'$ and $Y_3'$ are independently O, S or $NR_7'$;
$X_1'$ and $X_2'$ are independently OH or E;
$R_2'$, $R_3'$, $R_4'$, $R_5'$, $R_6'$, $R_7'$, $R_8'$, $R_9'$, $R_{10}'$ and $R_{11}'$ are independently selected from the group consisting of H, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
n' is zero or a positive integer; and
p' is zero or a positive integer.

3. A prodrug compound of the formula: $E'$-$R_1$-$E$ that releases an —SH-containing biologically active moiety wherein:
$R_1$ is a straight or branched residue of a water soluble polymer;

E is 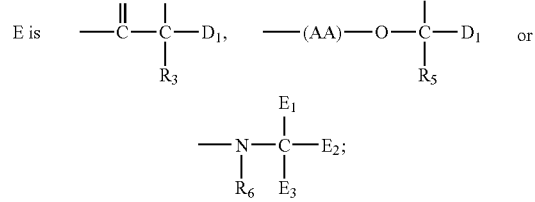

wherein:
$D_1$ is a residue of an —SH containing biologically active moiety bonded through the sulfur;
(AA) is an amino acid residue;

$E_1$ is 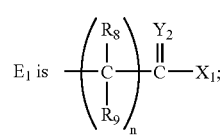

$E_2$ and $E_3$ are independently H, $E_1$ or

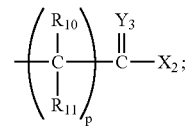

$Y_1$, $Y_2$ and $Y_3$ are independently O, S or $NR_7$;
$X_1$ and $X_2$ are independently OH or E;
$R_2$, $R_3$, $R_4$, $R_5$, $R_6$, $R_7$, $R_8$, $R_9$, $R_{10}$ and $R_{11}$ are independently selected from the group consisting of H, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
n is zero or a positive integer;
p is zero or a positive integer;

E' is E. 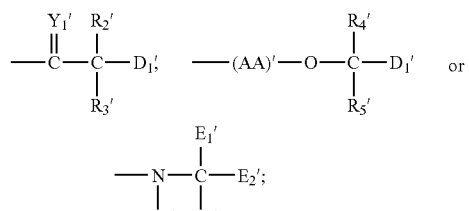

wherein:
$D_1'$ is a residue of a —SH containing moiety;
(AA)' is an amino acid residue;

$E_1'$ is 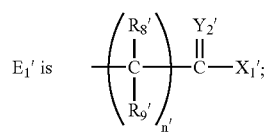

$E_2'$ and $E_3'$ are independently H, $E_1'$ or

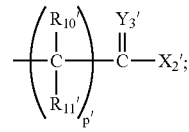

$Y_1'$, $Y_2'$ and $Y_3'$ are independently O, S or $NR_7'$;
$X_1'$ and $X_2'$ are independently OH or E;
$R_2'$, $R_3'$, $R_4'$, $R_5'$, $R_6'$, $R_7'$, $R_8'$, $R_9'$, $R_{10}'$ and $R_{11}'$ are independently selected from the group consisting of H, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
n' is zero or a positive integer; and
p' is zero or a positive integer.

4. The compound of claim 2, where n, n', p and p' are independently zero, one or two.

5. The compound of claim 1, wherein $R_2$ and $R_3$ are both H, n and p are both 2, $Y_1$ is O and both $E_1$ and $R_6$ are H.

6. The compound of claim 1, wherein $R_1$ comprises a polyalkylene oxide residue.

7. The compound of claim 6, wherein $R_1$ comprises a polyethylene glycol residue.

8. The compound of claim 1, wherein $R_1$ is
—C(=$Y_4$)—(CH$_2$)$_t$—O—(CH$_2$CH$_2$O)$_x$-A,
—C(=$Y_4$)—$Y_5$—(CH$_2$)$_t$—O—(CH$_2$CH$_2$O)$_x$-A,
—C(=$Y_4$)—NR$_{14}$—(CH$_2$)$_t$—O—(CH$_2$CH$_2$O)$_x$-A,
—(CR$_{15}$R$_{16}$)$_e$—O—(CH$_2$)$_t$—O—(CH$_2$CH$_2$O)$_x$-A,
—NR$_{14}$—(CH$_2$)$_t$—O—(CH$_2$CH$_2$O)$_x$-A,
—C(=$Y_4$)—(CH$_2$)$_t$—O—(CH$_2$CH$_2$O)$_x$—(CH$_2$)$_t$—C(=$Y_4$)—,
—C(=$Y_4$)—$Y_5$—(CH$_2$)$_t$—O—(CH$_2$CH$_2$O)$_x$—(CH$_2$)$_t$—$Y_5$—C(=$Y_4$)—,
—C(=$Y_4$)—NR$_{14}$—(CH$_2$)$_t$—O—(CH$_2$CH$_2$O)$_x$—(CH$_2$)$_t$—NR$_{14}$—C(=$Y_4$)—,
—(CR$_{15}$R$_{16}$)$_e$—O—(CH$_2$)$_t$—O—(CH$_2$CH$_2$O)$_x$—(CH$_2$)$_t$—O—(CR$_{15}$R$_{16}$)$_e$—, or
—NR$_{14}$—(CH$_2$)$_t$—O—(CH$_2$CH$_2$O)$_x$—(CH$_2$)$_t$—NR$_{14}$—
wherein:
x is the degree of polymerization;
$R_{14}$, $R_{15}$ and $R_{16}$ are independently selected from the group consisting of H, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
e and t are independently zero, one or two;
$Y_4$ and $Y_5$ are independently O, S or NR$_{12}$; and
A is a capping group.

9. The compound of claim 8, wherein A is selected from the group consisting of H, NH$_2$, OH, CO$_2$H and $C_{1-6}$ alkyls.

10. The compound of claim 1, wherein $R_1$ comprises —O—(CH$_2$CH$_2$O)$_x$ and x is a positive integer so that the weight average molecular weight is at least about 20,000.

11. The compound of claim 10, wherein $R_1$ has a weight average molecular weight of from about 20,000 to about 100,000.

12. The compound of claim 11, wherein $R_1$ has a weight average molecular weight of from about 25,000 to about 60,000.

13. The compound of claim 2, wherein $D_1$ and $D_1'$ are independently selected residues of SH-containing biologically active moieties.

14. The compound of claim 13, wherein said SH-containing moieties are selected from the group consisting of 1-β-D-ribofuranosyl, 1-β-D-arabinofuranosyl, penicillamine, 2-thiouracil, captopril, tiopronin, vasopressin, deaminooxytocin, thiopental sodium, and

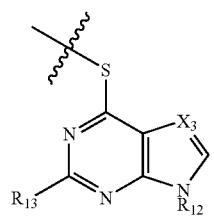

wherein
$R_{12}$ is H, a $C_{1-6}$ alkyl, alkoxy, or a carbohydrate of the formula:

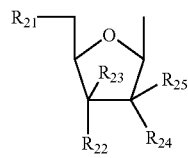

wherein $R_{21-25}$ are independently selected from the group consisting of alkoxy, OR$_{19}$, H, OH, N$_3$, NHR$_{20}$, NO$_2$, CN, fluoro, chloro, bromo, iodo, wherein $R_{19-20}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, halo, substituted aryls, aralkyls, $C_{1-6}$ heteroalkyls and substituted $C_{1-6}$ heteroalkyls;
$R_{13}$ is H or NH$_2$; and
$X_3$ is CH or N.

15. A compound of claim 3, selected from the group consisting of:

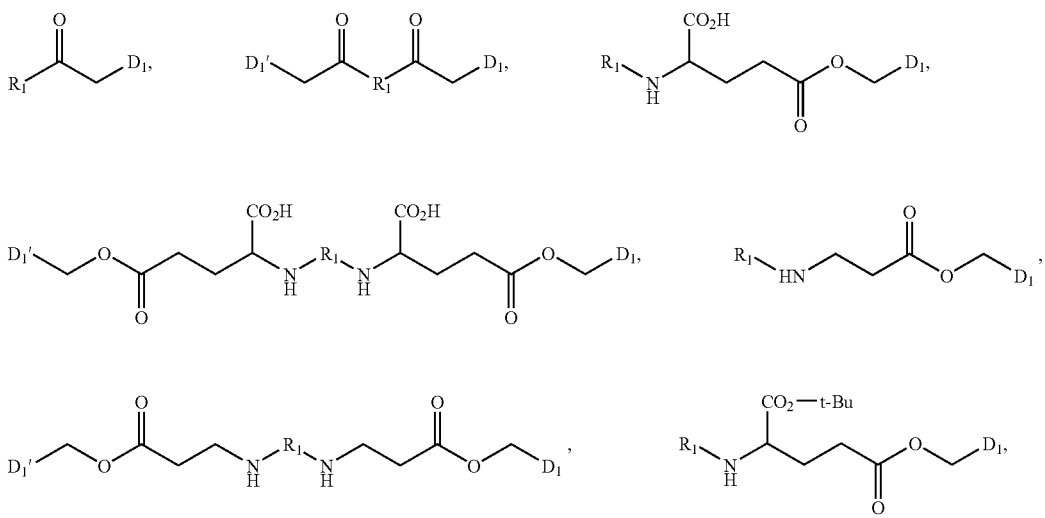

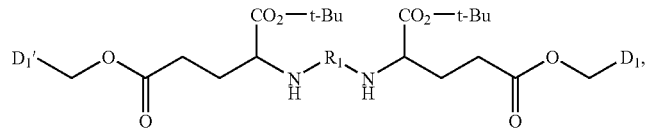
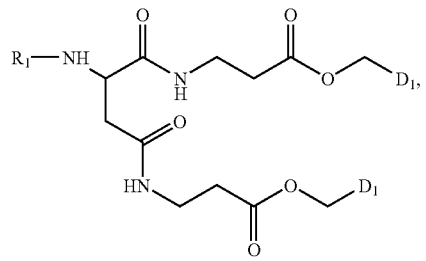
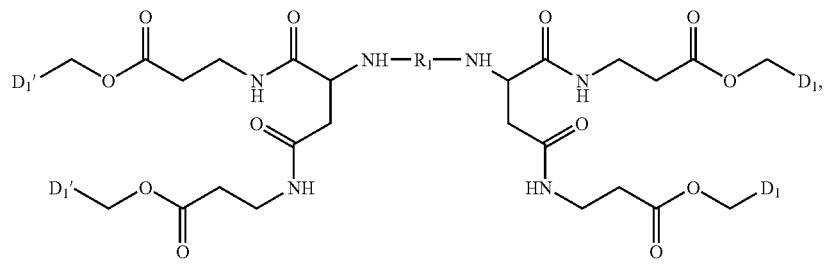
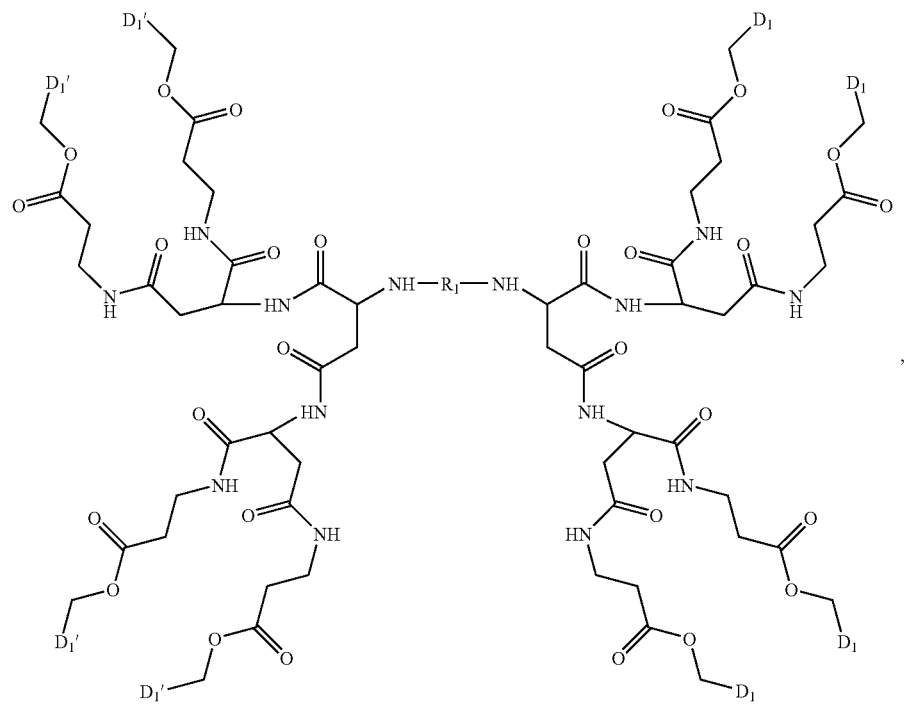

-continued
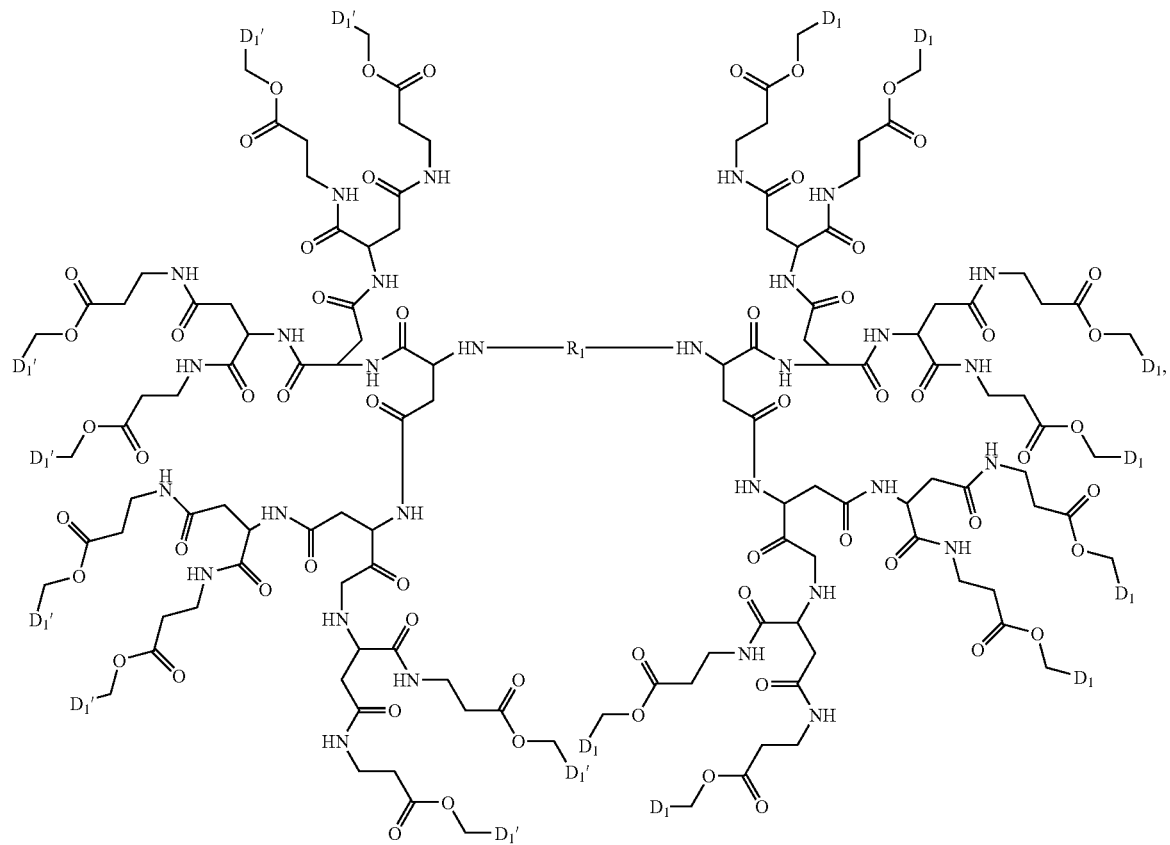
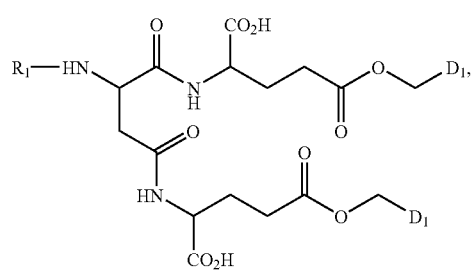
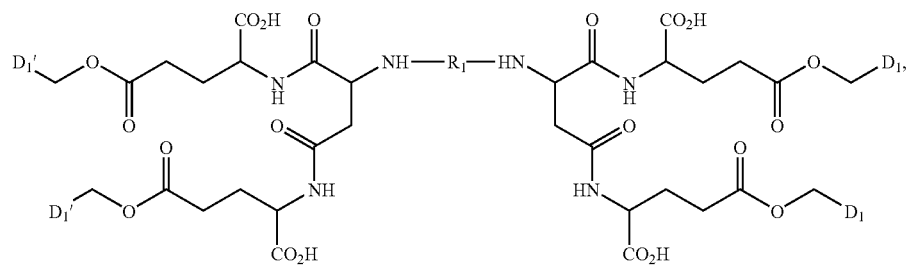

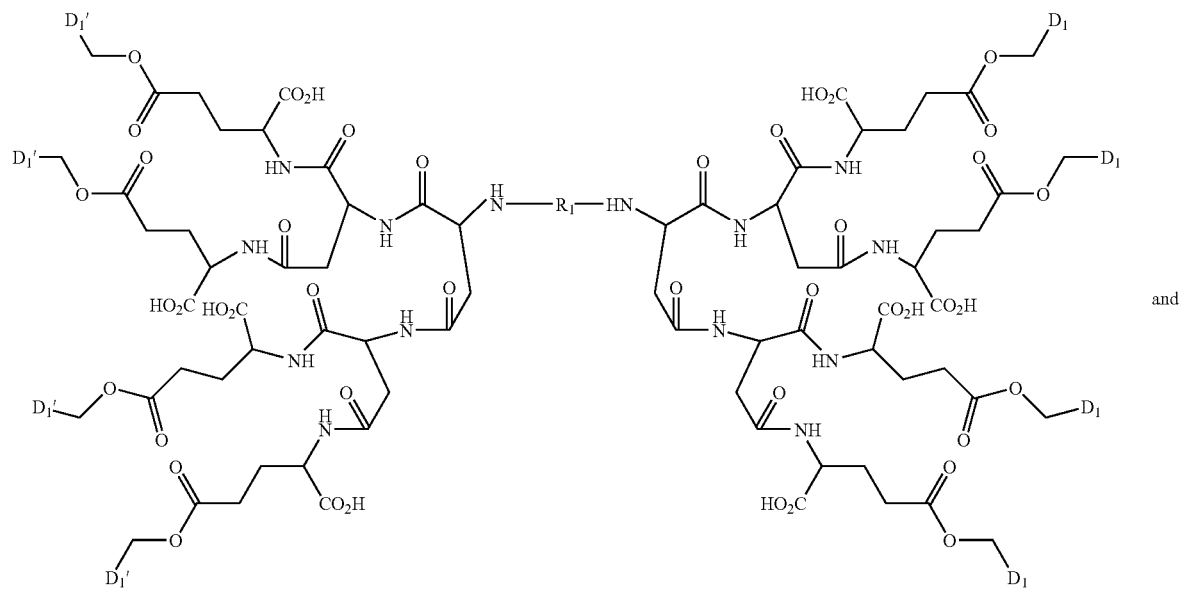
and
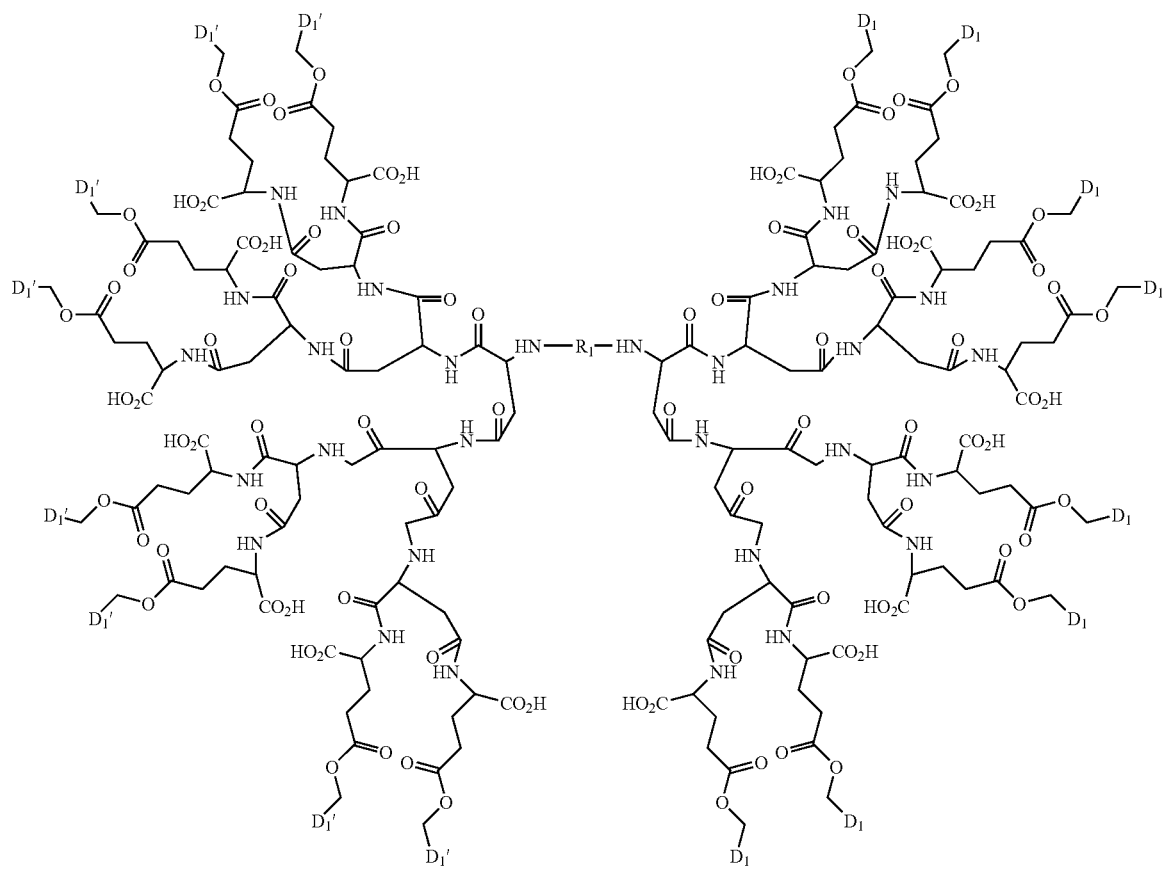

wherein:
R₁ is a straight or branched residue of a water soluble polymer and
D₁ and D₁' are residues of —SH containing biologically active moiety.

16. A method of treatment, comprising:
administering to a mammal in need of such treatment an effective amount of a compound of claim 1, wherein D₁ is a residue of a —SH containing biologically active moiety and the —SH containing biologically active moiety is released from R₁.

17. A method of treatment, comprising:
administering to a mammal in need of such treatment an effective amount of a compound of claim 3, wherein D₁ and D₁' are residues of a —SH containing biologically active moiety and the —SH containing biologically active moiety is released from R₁.

18. The compound of claim 1, wherein R₂ and R₃ are both H, and Y₁ is O.

19. A compound of claim 3 having the structure:

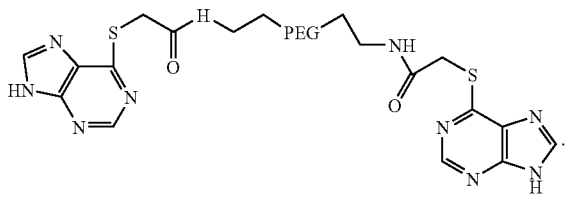

* * * * *